US009970000B2

(12) United States Patent
Kaehr et al.

(10) Patent No.: US 9,970,000 B2
(45) Date of Patent: May 15, 2018

(54) CELL-BASED COMPOSITE MATERIALS WITH PROGRAMMED STRUCTURES AND FUNCTIONS

(71) Applicants: National Technology & Engineering Solutions of Sandia, LLC, Albuquerque, NM (US); STC.UNM, Albuquerque, NM (US)

(72) Inventors: Bryan J. Kaehr, Albuquerque, NM (US); C. Jeffrey Brinker, Albuquerque, NM (US); Jason L. Townson, Seattle, WA (US)

(73) Assignee: National Technology Engineering Solutions of Sandia, LLC, Albuquerque, NM (US)

( * ) Notice: Subject to any disclaimer, the term of this patent is extended or adjusted under 35 U.S.C. 154(b) by 0 days. days.

(21) Appl. No.: 14/996,048

(22) Filed: Jan. 14, 2016

(65) Prior Publication Data
US 2016/0208238 A1 Jul. 21, 2016

Related U.S. Application Data

(62) Division of application No. 13/869,799, filed on Apr. 24, 2013, now Pat. No. 9,273,305.
(Continued)

(51) Int. Cl.
*C12N 11/14* (2006.01)
*C08K 3/36* (2006.01)
(52) U.S. Cl.
CPC ............... *C12N 11/14* (2013.01); *C08K 3/36* (2013.01)
(58) Field of Classification Search
None
See application file for complete search history.

(56) References Cited

U.S. PATENT DOCUMENTS

| 5,078,919 A | 1/1992 | Ashley et al. |
| 5,122,305 A | 6/1992 | Ashley et al. |

(Continued)

FOREIGN PATENT DOCUMENTS

| WO | WO 03/016040 A1 | 2/2003 |
| WO | WO 2008/060883 A2 | 5/2008 |

(Continued)

OTHER PUBLICATIONS

Campbell, Neil A; et al; Biology, 5th Ed., 136-139, 1999.*
(Continued)

*Primary Examiner* — David W Berke-Schlessel
(74) *Attorney, Agent, or Firm* — Helen S. Baca

(57) ABSTRACT

The present invention is directed to the use of silicic acid to transform biological materials, including cellular architecture into inorganic materials to provide biocomposites (nanomaterials) with stabilized structure and function. In the present invention, there has been discovered a means to stabilize the structure and function of biological materials, including cells, biomolecules, peptides, proteins (especially including enzymes), lipids, lipid vesicles, polysaccharides, cytoskeletal filaments, tissue and organs with silicic acid such that these materials may be used as biocomposites. In many instances, these materials retain their original biological activity and may be used in harsh conditions which would otherwise destroy the integrity of the biological material. In certain instances, these biomaterials may be storage stable for long periods of time and reconstituted after storage to return the biological material back to its original form. In addition, by exposing an entire cell to form CSCs, the CSCs may function to provide a unique system to study enzymes or a cascade of enzymes which are otherwise unavailable.

20 Claims, 20 Drawing Sheets

Related U.S. Application Data

(60) Provisional application No. 61/638,315, filed on Apr. 25, 2012.

(56) References Cited

U.S. PATENT DOCUMENTS

| | | | |
|---|---|---|---|
| 5,137,659 | A | 8/1992 | Ashley et al. |
| 5,151,110 | A | 9/1992 | Bein et al. |
| 5,224,972 | A | 7/1993 | Frye et al. |
| 5,240,647 | A | 8/1993 | Ashley et al. |
| 5,306,445 | A | 4/1994 | Reed et al. |
| 5,313,485 | A | 5/1994 | Hamil et al. |
| 5,565,142 | A | 10/1996 | Deshpande et al. |
| 5,589,396 | A | 12/1996 | Frye et al. |
| 5,770,275 | A | 6/1998 | Raman et al. |
| 5,772,735 | A | 6/1998 | Sehgal et al. |
| 5,858,457 | A | 1/1999 | Brinker et al. |
| 5,935,646 | A | 8/1999 | Raman et al. |
| 5,948,482 | A | 9/1999 | Brinker et al. |
| 5,949,071 | A | 9/1999 | Ruffner et al. |
| 6,057,377 | A | 5/2000 | Sasaki et al. |
| 6,258,305 | B1 | 7/2001 | Brinker et al. |
| 6,264,741 | B1 | 7/2001 | Brinker et al. |
| 6,270,846 | B1 | 8/2001 | Brinker et al. |
| 6,387,453 | B1 | 5/2002 | Brinker et al. |
| 6,471,761 | B2 | 10/2002 | Fan et al. |
| 6,495,352 | B1 | 12/2002 | Brinker et al. |
| 6,536,604 | B1 | 3/2003 | Brinker et al. |
| 6,808,867 | B2 | 10/2004 | Doshi et al. |
| 6,913,832 | B2 | 7/2005 | Fan et al. |
| 6,983,093 | B2 | 1/2006 | Fraval et al. |
| 7,332,264 | B2 | 2/2008 | Doshi et al. |
| 7,485,343 | B1 | 2/2009 | Branson et al. |
| 7,744,673 | B2 | 6/2010 | Jiang et al. |
| RE41,612 | E | 8/2010 | Brinker et al. |
| 7,947,579 | B2 | 5/2011 | Jiang et al. |
| 8,092,595 | B1 | 1/2012 | Fan et al. |
| 8,187,678 | B2 | 5/2012 | Jiang et al. |
| 8,246,933 | B2 | 8/2012 | Jiang et al. |
| 8,318,127 | B1 | 11/2012 | Jiang et al. |
| 8,501,057 | B1 | 8/2013 | Jiang et al. |
| 8,663,742 | B2 | 3/2014 | Kissel et al. |
| 8,859,190 | B1 | 10/2014 | Dirk et al. |
| 2011/0186971 | A1 | 8/2011 | Jiang et al. |
| 2011/0268791 | A1 | 11/2011 | Liu et al. |
| 2012/0040577 | A1 | 2/2012 | Kissel et al. |

FOREIGN PATENT DOCUMENTS

| | | | | |
|---|---|---|---|---|
| WO | WO 2011011468 | A2 * | 1/2011 | ............ C12N 11/14 |
| WO | WO 2012/149376 | A2 | 11/2012 | |
| WO | WO 2013/056132 | A2 | 4/2013 | |
| WO | WO 2013/103614 | A1 | 7/2013 | |

OTHER PUBLICATIONS

U.S. Appl. No. 12/903,577, filed Oct. 13, 2010, Brinker et al.
U.S. Appl. No. 12/909,572, filed Oct. 21, 2010, Brinker et al.
U.S. Appl. No. 13/253,964, filed Oct. 6, 2011, Brinker et al.
U.S. Appl. No. 13/484,139, filed May 30, 2012, Brinker et al.
U.S. Appl. No. 13/869,799, filed Apr. 24, 2013, Brinker et al.
U.S. Appl. No. 14/795,366, filed Jul. 9, 2015, Kaehr et al.
Ashley CE et al., "Cell-specific delivery of diverse cargos by bacteriophage MS2 virus-like particles," *ACS Nano* Jul. 26, 2011;5(7):5729-45.
Ashley CE et al., "The targeted delivery of multicomponent cargos to cancer cells by nanoporous particle-supported lipid bilayers," *Nat. Mater.* May 2011;10(5):389-97.
Avnir D et al., "Recent bio-applications of sol-gel materials," *J. Mater. Chem.* 2006;16:1013-30.
Baca HK et al., "Cell-directed-assembly: Directing the formation of nano/bio interfaces and architectures with living cells," *Biochim. Biophys. Acta* Mar. 2011;1810(3):259-67.
Baca HK et al., "Cell-directed assembly of bio/nano interfaces—A new scheme for cell immobilization," *Acc. Chem. Res.* Sep. 2007;40(9):836-45.
Baca HK et al., "Cell-directed assembly of lipid-silica nanostructures providing extended cell viability," *Science* Jul. 21, 2006;313(5785):337-41.
Bao Z et al., "Chemical reduction of three-dimensional silica micro-assemblies into microporous silicon replicas," *Nature* Mar. 2007;446:172-5.
Bassindale et al., "Simple and mild preparation of silica-enzyme composites from silicic acid solution," *J. Mater. Chem.* 2009;19:7606-9.
Beck JS et al., "A new family of mesoporous molecular sieves prepared with liquid crystal templates," *J. Am. Chem. Soc.* 1992;114(27):10834-43.
Betancor L et al., "Bioinspired enzyme encapsulation for biocatalysis," *Trends Biotechnol.* Aug. 2008;26(10):566-72.
Boissiere C et al., "Aerosol route to functional nanostructured inorganic and hybrid porous materials," *Adv. Mater.* 2011;23:599-623.
Braet F et al., "Drying cells for SEM, AFM and TEM by hexamethyldisilazane: A study on hepatic endothelial cells," *J. Microsc.* Apr. 1997;186(1):84-7.
Bray DF et al., "Comparison of hexamethyldisilazane (HMDS), Peldri II and critical-point drying methods for scanning electron microscopy of biological specimens," *Microsc. Res. Tech.* 1993;26:489-95.
Brinker CJ et al., "Evaporation-induced self-assembly: Nanostructures made easy," *Adv. Mater.* May 1999;11(7):579-85.
Brunner E et al., "Chitin-based organic networks: An integral part of cell wall biosilica in the diatom *Thalassiosira pseudonana*," *Angew. Chem. Int. Ed. Engl.* 2009;48:9724-7.
Carroll NJ et al., "Microparticles with bimodal nanoporosity derived by microemulsion templating," *Langmuir* 2009;25(23):13540-4.
Cha JN et al., "Silicatein filaments and subunits from a marine sponge direct the polymerization of silica and silicones in vitro," *Proc. Nat'l Acad. Sci. USA* Jan. 1999;96:361-5.
Chen CL et al., "Peptide-based methods for the preparation of nanostructured inorganic materials," *Angew. Chem. Int. Ed. Engl.* Mar. 8, 2010;49(11):1924-42.
Chen Z et al., "DNA translocation through an array of kinked nanopores," *Nat. Mater.* Aug. 2010;9(8):667-75.
Coradin T et al., "Interactions of bovine serum albumin and lysozyme with sodium silicate solutions," *Colloids Surf. B* 2003;29:189-96.
Dengler EC et al., "Mesoporous silica-supported lipid bilayers (protocells) for DNA cargo delivery to the spinal cord," *J. Control. Release* Jun. 10, 2013;168(2):209-24.
Dickerson MB et al., "Protein- and peptide-directed syntheses of inorganic materials," *Chem. Rev.* 2008;108:4935-78.
Fratzl P et al., "Bio-inspired materials—Mining the old literature for new ideas," *Adv. Mater.* 2010;22:4547-50.
Gautier C et al., "Biomimetic dual templating of silica by polysaccharide/protein assemblies," *Colloids Surf. B* 2008;65:140-5.
Hanefeld U et al., "Understanding enzyme immobilisation," *Chem. Soc. Rev.* Feb. 2009;38(2):453-68.
Harper JC et al., "Biocompatible microfabrication of 3D isolation chambers for targeted confinement of individual cells and their progeny," *Anal. Chem.* Oct. 2012;84(21):8985-9.
Harper JC et al., "Cell-directed integration into three-dimensional lipid—Silica nanostructured matrices," *ACS Nano* Oct. 26, 2010;4(10):5539-50.
Harper JC et al., "Encapsulation of *S. cerevisiae* in poly(glycerol) silicate derived matrices: Effect of matrix additives and cell metabolic phase on long-term viability and rate of gene expression," *Chem. Mater.* Apr. 2011;23(10):2555-64.
Harper JC et al., "Orthogonal cell-based biosensing: Fluorescent, electrochemical, and colorimetric detection with silica-immobilized cellular communities integrated with an ITO-glass/plastic laminate cartridge," *Small* Sep. 10, 2012;8(17):2743-51.
Hatton B et al., "Assembly of large-area, highly ordered, crack-free inverse opal films," *Proc. Nat'l Acad. Sci. USA* 2010;107:10354-9.

(56) References Cited

OTHER PUBLICATIONS

Hildebrand M et al., "Application of AFM in understanding biomineral formation in diatoms," *Pflügers Arch.* 2008;456:127-37.
Hildebrand M, "Diatoms, biomineralization processes, and genomics," *Chem. Rev.* 2008;108:4855-74.
Hildebrand M, "Prospects of manipulating diatom silica nanostructure," *J. Nanosci. Nanotechnol.* 2005;5:146-57.
Holland BT et al., "Synthesis of macroporous minerals with highly ordered three-dimensional arrays of spheroidal voids," *Science* Jul. 1998;281:538-40.
Hudson S et al., "Proteins in mesoporous silicates," *Angew. Chem. Int. Ed. Engl.* 2008;47:8582-94.
Jiang X et al., "Aerosol-assisted synthesis of monodisperse single-crystalline α-cristobalite nanospheres," *Chem. Commun. (Camb.)* Jan. 30, 2012;48(9):1293-5.
Jiang X et al., "Aerosol fabrication of hollow mesoporous silica nanoparticles and encapsulation of L-methionine as a candidate drug cargo," *Chem. Commun. (Camb.)* May 7, 2010;46(17):3019-21.
Jiang X et al., "Hydrothermal synthesis of monodisperse single-crystalline alpha-quartz nanospheres," *Chem. Commun. (Camb.)* Jul. 14, 2011;47(26):7524-6.
Jiang X et al., "Photoresponsive release from azobenzene-modified single cubic crystal NaCl/silica particles," *J. Nanomater.* 2011; Art. No. 439756 (6 pages).
Johnson P et al., "Nano-engineered, ultra stable, live cell vaccines against tuberculosis," 2011, 1 page (available from http://posterhall.org/system/igert/igert2011/posters/146/presentations/2011_IGERT_final_-_PJohnson.pdf?1302924782, last accessed Apr. 20, 2014).
Kaehr B et al., "Cellular complexity captured in durable silica biocomposites," *Proc. Nati Acad. Sci. USA* Oct. 23, 2012;109(43):17336-41.
Kaehr B et al., Supporting information for "Cellular complexity captured in durable silica biocomposites," *Proc. Nat'l Acad. Sci. USA* Oct. 23, 2012;109(43):17336-41, available at http://www.pnas.org/content/109/43/17336.long?tab=ds (last accessed May 1, 2014) (6 pages).
Khripin CY et al., "Protein-directed assembly of arbitrary three-dimensional nanoporous silica architectures," *ACS Nano* 2011;5(2):1401-9.
Khripin CY et al., Supporting information for "Protein-directed assembly of arbitrary three-dimensional nanoporous silica architectures," *ACS Nano* 2011;5(2)1401-9, available at http://pubs.acs.org/doi/suppl/10.1021/nn1031774 (last accessed May 1, 2014) (7 pages).
Kresge CT et al., "Ordered mesoporous molecular sieves synthesized by a liquid-crystal template mechanism," *Nature* Oct. 1992;359:710-2.
Kröger N, "Prescribing diatom morphology: Toward genetic engineering of biological nanomaterials," *Curr. Opin. Chem. Biol.* 2007;11:662-9.
Kröger N et al., "Polycationic peptides from diatom biosilica that direct silica nanosphere formation," *Science* 1999;286:1129-32.
Kröger N et al., "Self-assembly of highly phosphorylated silaffins and their function in biosilica morphogenesis," *Science* 2002;298:584-6.
Kröger N et al., "Species-specific polyamines from diatoms control silica morphology," *Proc. Nat'l Acad. Sci. USA* 2000;97(26):14133-8.
Liu J et al., "Electrostatically mediated liposome fusion and lipid exchange with a nanoparticle-supported bilayer for control of surface charge, drug containment, and delivery," *J. Am. Chem. Soc.* Jun. 10, 2009;131(22):7567-9.
Liu J et al., "Porous nanoparticle supported lipid bilayers (protocells) as delivery vehicles," *J. Am. Chem. Soc.* Feb. 4, 2009;131(4):1354-5.
Losic D et al., "Diatomaceous lessons in nanotechnology and advanced materials," *Adv. Mater.* 2009;21:2947-58.
Lu Y et al., "Aerosol-assisted self-assembly of mesostructured spherical nanoparticles," *Nature* Mar. 1999;398:223-6.
Lu Y et al., "Evaporation-induced self-assembly of hybrid bridged silsesquioxane film and particulate mesophases with integral organic functionality," *J. Am. Chem. Soc.* 2000;122(22):5258-61.
Mann Set al., "Synthesis of inorganic materials with complex form," *Nature* Jul. 1996;382:313-8.
Meunier CF et al., "Encapsulation of cells within silica matrixes: Towards a new advance in the conception of living hybrid materials," *J. Colloid Interface Sci.* 2010;342:211-24.
Meyer KC et al., "Mechanically encoded cellular shapes for synthesis of anisotropic mesoporous particles," *J. Am. Chem. Soc.* 2014;136:13138-41.
Meyer KC et al., Supporting information for "Mechanically encoded cellular shapes for synthesis of anisotropic mesoporous particles," *J. Am. Chem. Soc.* 2014;136:13138-41 (10 pages).
Moghaddam S et al., "An inorganic-organic proton exchange membrane for fuel cells with a controlled nanoscale pore structure," *Nat. Nanotechnol.* Mar. 2010;5(3):230-6.
Niu L et al., "Infiltration of silica inside fibrillar collagen," *Angew. Chem. Int. Ed. Engl.* 2011;50:11688-91.
Paris O et al., "Biomimetics and biotemplating of natural materials," *MRS Bull.* 2010;35:219-25.
Patwardhan SV et al., "On the role(s) of additives in bioinspired silicification," *Chem. Commun.* 2005;9:1113-21.
Pouget E et al., "Hierarchical architectures by synergy between dynamical template self-assembly and biomineralization," *Nat. Mater.* 2007;6:434-9.
Rempe S et al., "Biomimetic membranes for water purification," Sandia Report No. SAND2011-2061P, 2011 (28 pages).
Scheffel A et al., "Nanopatterned protein microrings from a diatom that direct silica morphogenesis," *Proc. Nat'l Acad. Sci. USA* 2011;108:3175-80.
Shopsowitz KE et al., "Free-standing mesoporous silica films with tunable chiral nematic structures," *Nature* 2010;468:422-5.
Stein A et al., "Morphological control in colloidal crystal templating of inverse opals, hierarchical structures, and shaped particles," *Chem. Mater.* 2008;20:649-66.
Tesson B et al., "Extensive and intimate association of the cytoskeleton with forming silica in diatoms: Control over patterning on the meso- and micro-scale," *PloS One* 2010;5:e14300 (13 pages).
Townley HE et al., "Modification of the physical and optical properties of the frustule of the diatom *Coscinodiscus wailesii* by nickel sulfate," *Nanotechnology* 2007;18:295101-6.
Townson JL et al., "Synthetic fossilization of soft biological tissues and their shape-preserving transformation into silica or electron-conductive replicas," *Nat. Commun.* Dec. 2014;5:5665 (5 pp.).
Townson JL et al., Supporting information for "Synthetic fossilization of soft biological tissues and their shape-preserving transformation into silica or electron-conductive replicas," *Nat. Commun.* Dec. 2014;5:5665 (8 pp.).
van Bommel KJC et al., "Organic templates for the generation of inorganic materials," *Angew. Chem. Int. Ed. Engl.* 2003;42(9):980-99.
Van Opdenbosch D et al., "Silica replication of the hierarchical structure of wood with nanometer precision," *J. Mater. Res.* May 2011;26(10):1193-202.
Warnock JN et al., "Bioreactor systems for the production of biopharmaceuticals from animal cells," *Biotechnol. Appl. Biochem.* 2006;45:1-12.
Wei Y et al., "A novel method for enzyme immobilization: direct encapsulation of acid phosphatase in nanoporous silica host materials," *J. Nanosci. Nanotechnol.* Mar. 2001;1(1):83-93.
Wei Y et al., "Preparation and physisorption characterization of D-glucose-templated mesoporous silica sol-gel materials," *Chem. Mater.* 1999;11:2023-9.
Wilson BS, et al., "Calcium-dependent clustering of inositol 1,4,5-trisphosphate receptors," *Mol. Biol. Cell* Jun. 1998;9:1465-78.
Xing Z et al., "Scale-up analysis for a CHO cell culture process in large-scale bioreactors," *Biotechnol. Bioeng.* Jul. 2009;103(4):733-46.

(56) References Cited

OTHER PUBLICATIONS

Kaehr B, "Development and characterization of 3D, nano-confined multicellular constructs for advanced biohybrid devices," *Sandia Report SAND2011-6892*, Sep. 2011 (24 pp.).

* cited by examiner

CELL-BASED COMPOSITE MATERIALS WITH PROGRAMMED STRUCTURES AND FUNCTIONS

CROSS-REFERENCE TO RELATED APPLICATION

This application claims the benefit of U.S. Provisional Application No. 61/638,315, filed Apr. 25, 2012, which is incorporated herein by reference in its entirety. This application is also a divisional of prior application Ser. No. 13/869,799, filed Apr. 24, 2013, which is also incorporated herein by reference in its entirety.

STATEMENT OF GOVERNMENT INTEREST

This invention was made with Government support under contract no. DE-AC04-94AL85000 awarded by the U. S. Department of Energy to Sandia Corporation. The Government has certain rights in the invention.

FIELD OF THE INVENTION

The present invention relates to cell-based composite materials and, in particular, to cell-based composite materials with programmed structures and functions.

BACKGROUND OF THE INVENTION

The synthesis of inorganic materials with controlled and complex forms has been facilitated through discoveries such as vesicle, micelle and liquid crystalline templating of silicates which provided inspiration to explore a range of templating strategies based on self-assembled molecular precursors, colloids, and biological templates and vessels. See C. T. Kresge et al., *Nature* 359, 710 (1992); J. S. Beck et al., *J Am Chem Soc* 114, 10834 (1992); S. Mann and G. A. Ozin, *Nature* 382, 313 (1996); C. J. Brinker et al., *Adv Mater* 11, 579 (1999); E. Pouget et al., *Nat Mater* 6, 434 (2007); C. L. Chen and N. L. Rosi, *Angew Chem Int Ed* 49, 1924 (2010); K. E. Shopsowitz et al., *Nature* 468, 422 (2010); C. Boissiere et al., *Adv Mater* 23, 599 (2011); B. T. Holland et al., *Science* 281, 538 (1988); B. Hatton et al., *Proc Natl Acad Sci USA* 107, 10354 (2010); A. Stein et al., *Chem Mater* 20, 649 (2008); O. Paris et al., *MRS Bull* 35, 219 (2010); D. Van Opdenbosch et al., *J Mater Chem* 26, 1193 (2011); and K. J. C. van Bommel et al., *Angew Chem Int Ed* 42(9), 980 (2003). A driving force for these efforts is the many complex inorganic structures found in nature. An oft-cited example is the hierarchical composites built by silica condensing microorganisms such as diatoms, which have generated substantial scientific interest for over a century. See P. Fratzl and S. Weiner et al., *Adv Mater* 22, 4547 (2010). Diatoms display complex 3D architectures with great structural control over nano- to millimeter length scales. However, despite some success toward elucidating mechanisms of diatom biomineralization, the in vitro synthesis of 3D diatom-like forms has remained elusive. Diatom silica has found numerous applications including as a chemical stabilizer, absorbent, filter medium, and fine abrasive, and the lack of synthetic analogues has facilitated recent investigations to employ diatom frustules as starting materials for shape-preserving chemical transformations into functional nanomaterials. See K. H. Sandhage et al., *Handbook of Biomineralization: Biomimetic and bioinspired chemistry*, 235 (2007); D. Losic et al., *Adv Mater* 21, 2947 (2009); and Z. Bao et al., *Nature* 446, 172 (2007).

Given the potential of this biosilica, it would be desirable to be able to wield control over the silica structure in order to achieve broader applicability; however, strategies to direct diatom morphology using chemical and genetic approaches has proven challenging. See M. Hildebrand, *J Nanosci Nanotechno* 5, 146 (2005); H. E. Townley et al., *Nanotechnology* 18, 295101 (2007); and N. Kroger, *Curr Opin Chem Biol* 11, 662 (2007). Therefore, an ability to generate cell frustules from more malleable templates such as mammalian cells would provide greater access to natural and engineered cell heterogeneity—both structure and function—to be exploited in the design of complex materials.

To these ends, biomineralization by silica condensing microorganisms offers key lessons. The discovery of biogenic peptides that catalyze silica condensation subsequently has motivated the extensive investigation of the interaction of natural and synthetically-derived peptides and proteins with silica and its precursors. See N. Kroger et al., *Proc Natl Acad Sci USA* 97, 14133 (2000); N. Kroger et al., *Science* 286, 1129 (1999); J. N. Cha et al., *Proc Natl Acad Sci USA* 96, 361 (1999); E. Pouget et al., *Nat Mater* 6, 434 (2007); N. Kroger et al., *Science* 298, 584 (2002); T. Coradin et al., *Colloids Surf B* 29, 189 (2003); A. Bassindale et al., *J Mater Chem* 19, 7606 (2009); C. Gautier et al., *Colloids Surf B* 65, 140 (2008); M. Dickerson et al., *Chem Rev* 108, 4935 (2008); and S. V. Patwardhan et al., *Chem Commun* 9, 1113 (2005). Identification of silica associated biomolecules such as long-chain polyamines and the silaffin peptides has led to a general understanding of the tenets by which macromolecules control polymerization of silica precursors into silica assemblies. See N. Kroger et al., *Proc Natl Acad Sci USA* 97, 14133 (2000); N. Kroger et al., *Science* 286, 1129 (1999); and M. Hildebrand, *Chem Rev* 108, 4855 (2008). However, silica morphogenesis at the meso- and micro-scales must involve both transport of soluble silica precursors and their directed deposition by biomolecular templating or structural elements. See B. Tesson and M. Hildebrand, *PloS one* 5, e14300 (2010); E. Brunner et al., *Angew Chem Int Ed* 48, 9724 (2009); and A. Scheffel et al., *Proc Natl Acad Sci USA* 108, 3175 (2011). Likely, these larger scale molecular assemblies direct the assembly of silica building blocks, formed in the silica deposition vesicle (SDV), into complex structures.

Therefore, Khripin et al. recently examined whether synthetic 3D protein scaffolds could direct/template silica deposition provided the appropriate silica precursors and chemical conditions. See C. Y. Khripin et al., *ACS Nano* 5, 1401 (2011). They showed that microfabricated protein hydrogels could template silica volumetrically into mechanically stable, nano- to micro-scale biocomposites with user-defined 3D features identical in size and shape to those of the template. These features were preserved following removal of the organic component to form a porous silica replica. Importantly, proteins of diverse properties (e.g., isoelectric point; pI) directed silica condensation under identical solution conditions (100 mM silicic acid, pH 3), which is somewhat contrary to the generally held understanding that cationic species (e.g., proteins with pI>7) are required for biogenic silica deposition. See A. Bassindale et al., *J Mater Chem* 19, 7606 (2009). These protein hydrogels are highly concentrated (>40% protein by wt vol$^{-1}$), producing a locally crowded 3D molecular environment, which acts to capture and concentrate silica precursors (mono-, oligo-silicic acid, and nanoparticles) via hydrogen bonding and other non-covalent interactions, promoting their further condensation and conversion to covalently bonded siloxane replicas.

However, a need remains for a method of directed silica condensation in naturally crowded molecular environments, such as cells, under similar conditions.

SUMMARY OF THE INVENTION

The present invention is directed to the use of silicic acid to transform biological materials, including cellular architecture into inorganic materials to provide biocomposites (nanomaterials) with stabilized structure and function. In the present invention, there has been discovered a means to stabilize the structure and function of biological materials, including cells, biomolecules, peptides, proteins (especially including enzymes), lipids, lipid vesicles, polysaccharides, cytoskeletal filaments, tissue and organs with silicic acid such that these materials may be used as biocomposites. In many instances, these materials retain their original biological activity and may be used in harsh conditions which would otherwise destroy the integrity of the biological material. In certain instances, these biomaterials may be storage stable for long periods of time and reconstituted after storage to return the biological material back to its original form. In addition, by exposing an entire cell to form CSCs, the CSCs may function to provide a unique system to study enzymes or a cascade of enzymes which are otherwise unavailable.

The present invention is more particularly directed to a method to synthesize cell/silica composites, comprising incubating a plurality of cells in a silicic acid solution to provide cell/silica composite particles. The plurality of cells can comprise mammalian cells, prokaryotic cells, plant cells, cultured cells, or even tissue or other multicellular organisms. The plurality of cells can be genetically, chemically, or physically modified. The method can further comprise fixing the plurality of cells in a fixative prior to the incubating step. The silicic acid solution is preferably osmotically balanced (isotonic). The silicification can be performed in a suspension and the resulting cell/silica composite particles can be dehydrated to provide monodisperse cell/silica composite particles. Alternatively, the cells can be plated or patterned on a substrate prior to incubation. The method can further comprise calcinating the cell/silica composite particles at an elevated temperature to provide silica replicas. The silicified cells can be used for the replication of biological surfaces. For example, the method can further comprise reconstituting a cellular function on the silica replicas, such as by introducing an amphiphilic lipid bilayer on the outer surface of the silica replicas and by the addition of biological material (e.g., enzymes, ATP, organelles, RNA, etc.). Therefore, the silicified cells can provide a substrate for 3D cell culture, cell interaction and differentiation, or tissue regeneration. The substrate can be de-silicified to enable stable, long-term preservation of biological material. The method can further comprise pyrolyzing the cell-silica composite particles at a high temperature in an inert atmosphere to provide carbonized-cell/silica composite particles. The carbonized particles can be electrically conductive or provide a conductive support. For example, the carbonized-cell/silica composite particles provide a biocatalyst. For example, the cell/silica composites, silica replicas, or carbonized-cell/silica composite particles can provide a separation medium, adsorbent, or absorbent.

Tissue-derived cultured cells exhibit a remarkable range of morphological features in vitro, depending on phenotypic expression and environmental interactions. Translation of these cellular architectures into inorganic materials according to the present invention provides new routes to generate hierarchical nanomaterials with stabilized structures and functions. As an example, the fabrication of cell/silica composites (CSCs) and their conversion to silica replicas using mammalian cells as scaffolds to direct complex structure formation is described herein. Under mildly acidic solution conditions, silica deposition is restricted to the molecularly crowded cellular template. Inter- and intracellular heterogeneity from the nano- to macro-scale is captured and dimensionally preserved in CSCs following drying and subjection to extreme temperatures allowing, for instance, size and shape preserving pyrolysis of cellular architectures to form conductive carbon replicas. The structural and behavioral malleability of the starting material (cultured cells) provides opportunities to develop robust and economical biocomposites with programmed structures and functions.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Figure 1:
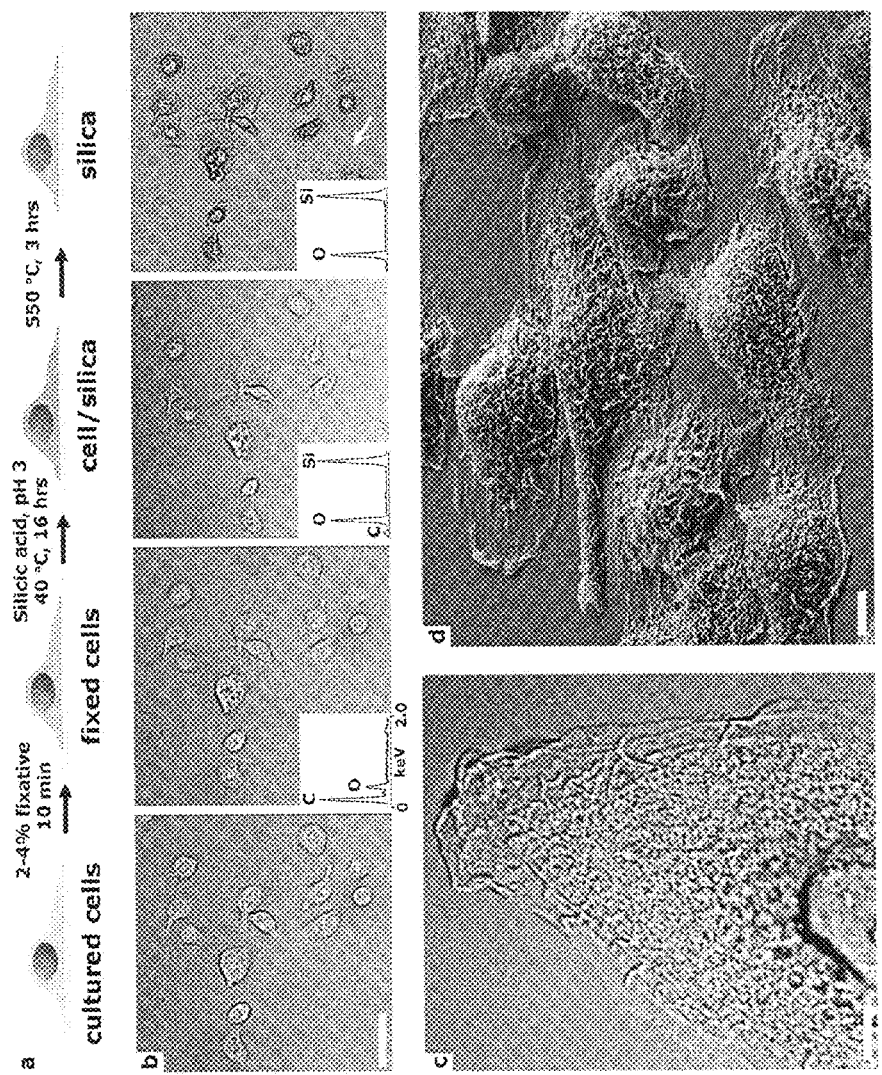
FIG. 1 shows silicification of mammalian cells cultured on flat substrates. Provided are (a) a schematic describing the process of cell silicification; and (b) an optical image field of AsPC-1 cells throughout the steps shown in (a) of silicification. Images in panels 1 and 2 show hydrated cells and panels 3 and 4 show dehydrated composites and silica replicas. Insets show representative EDS spectra of cells at the various stages. Provided are (c) a close-up differential interference contrast (DIC) image of the cell noted by the white arrow in b, rightmost panel; and (d) a representative SEM image of AsPC-1 templated cell silica following calcination. Scale bars: 40 μm (b); 5 μm (c and d).

In accordance with the present invention there may be employed conventional chemical synthetic methods and other biological techniques within the skill of the art. Such techniques are well-known and are otherwise explained fully in the literature.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "and" and "the" include plural references unless the context clearly dictates otherwise.

Furthermore, the following terms shall have the definitions set out below. It is understood that in the event a specific term is not defined herein below, that term shall have a meaning within its typical use within context by those of ordinary skill in the art.

The term "compound", as used herein, unless otherwise indicated, refers to any specific chemical compound disclosed herein. Within its use in context, the term generally refers to a single silicic acid compound or it's analog or derivative. In certain instances the term may also refer to stereoisomers and/or optical isomers (including racemic mixtures) or enantiomerically enriched mixtures of disclosed compounds.

The term "effective" is used herein, unless otherwise indicated, to describe an amount or concentration of a compound or composition which, in context, is used to produce or affect an intended result.

The term "silicic acid" shall mean a family of chemical compounds containing the element silicon attached to oxide and hydroxyl groups which are capable of condensing and forming oligomeric and/or polymeric silicon dioxide coatings pursuant to the present invention. This family of compounds includes at least one compound selected from the group consisting of orthosilicic acid (generally referred to as silicic acid), metasilicic acid, disilic acid and pyrosilicic acid, among others. Two silicic acid derivatives which find use in the present invention include tetramethoxysilane (TMOS), tetraethoxysilane (TEOS) and mixtures thereof and are used as preferred silicic acid compounds according to the present invention because of their ready availability and the ease with which they may be used and controlled in solution. The silicic acid compounds are generally used in a dilute, weak acid solution to provide silicone dioxide coatings onto structures which are found in the biological materials which are exposed to the process according to the present invention.

The term "dehydration" is used to describe a simple process by which the CSCs which are produced are dehydrated to remove any excess water. Dehydration may be performed by simply adding a solvent such as methanol, ethanol, or another volatile solvent is used to remove any excess water. In addition, the CSCs produced may be simply air dried at room or slightly elevated temperature to remove water. Any process to remove water without impacting the structure of function of the CSCs produced may be used in the dehydration step.

The term "reconstitution" shall refer to the ability of the CSCs according to the present invention to be reconstituted as biological material from the silicone dioxide coated compositions. CSCs according to the invention are coated with polymeric silicone dioxide pursuant to exposure to silicic acid as disclosed herein. The silicic acid will form a polymeric coating of silicon dioxide on the biological surfaces of the material which are exposed to the silicic acid to produce CSCs. Upon exposure of the CSCs to solution (e.g., saline solution, buffered solution, a weak base solution or a dilute solution of HF, among others), the CSCs may be reconstituted back to their original biological state.

The term "storage stable" shall mean storage for a period of at least a few days, preferably, at least several weeks, months or even years in a CSC form, which can be readily reconstituted in solution as described above, The term "calcination" is used to describe a step to remove organic materials from the CSCs produced using the present method. Calcination occurs at elevated temperature (about 500-650° C. for a period of several hours sufficient to remove organic material from the CSCs, resulting in a three dimensional structure of silicon dioxide which remains after much of the biological material is removed from the CSC.

The present invention is directed to a generalized route to synthesize cell/silica composites (CSCs), analogous to diatom frustules, using cells and other biological material including collections of cells, tissue, organs and related biological material as scaffolds directing complex structure formation. Inter- and intracellular heterogeneity from the nano- to macroscale is captured and dimensionally preserved in CSCs following drying and high temperature processing allowing, for instance, size and shape preserving pyrolysis of cellular architectures to form conductive carbon replicas. The structural and behavioral malleability of the starting material provides vast opportunities to develop robust and economical biocomposites with programmed structures and functions.

In the present invention, a biological material is exposed to a silicification step comprising exposing the biological material to silicic acid (or one or more of its derivatives and/or analogs such as tetramethoxy silane and/or tetraethoxysilane at an effective concentration (preferably ranging from about 50-250 mM, about 100 mM, or as otherwise described herein) in an aqueous solvent (including a buffered solvent), at a pH ranging from about 1.5-4.5 (preferably about 3) in acid solution at low temperature (generally, less than about 0° C., preferably less than about 20° C., less than about 30° C., less than about 40° C. for a period sufficient (preferably, a few hours to about 24 hours, preferably, about 8-15 hours) to produce cell/silica composition (CSC) material particles comprising primarily silicon, oxygen and carbon, optionally, dehydrating the CSC produced from the first step; and optionally calcinating the CSC particles at elevated temperature (generally, at about 500-650 C, preferably about 550-600 C for several hours, preferably about 3-4 hours, in air) to produce calcinated CSC. It is noted that the dehydration step and the calcination are not required; rather the CSCs once formed, may be simply removed from the silicic acid, washed with solvent and used. In addition, the dehydration step is often not utilized when the CSCs which are produced are subject to the calcination step—given that the conditions of calcination will tend to dehydrate the CSC particles. Accordingly, when CSC are not calcinated, for example, when it is found desirable to maintain at least some of the organics in the CSCs produced, a dehydration step is often used in the absence of a calcination step.

Figure 19:
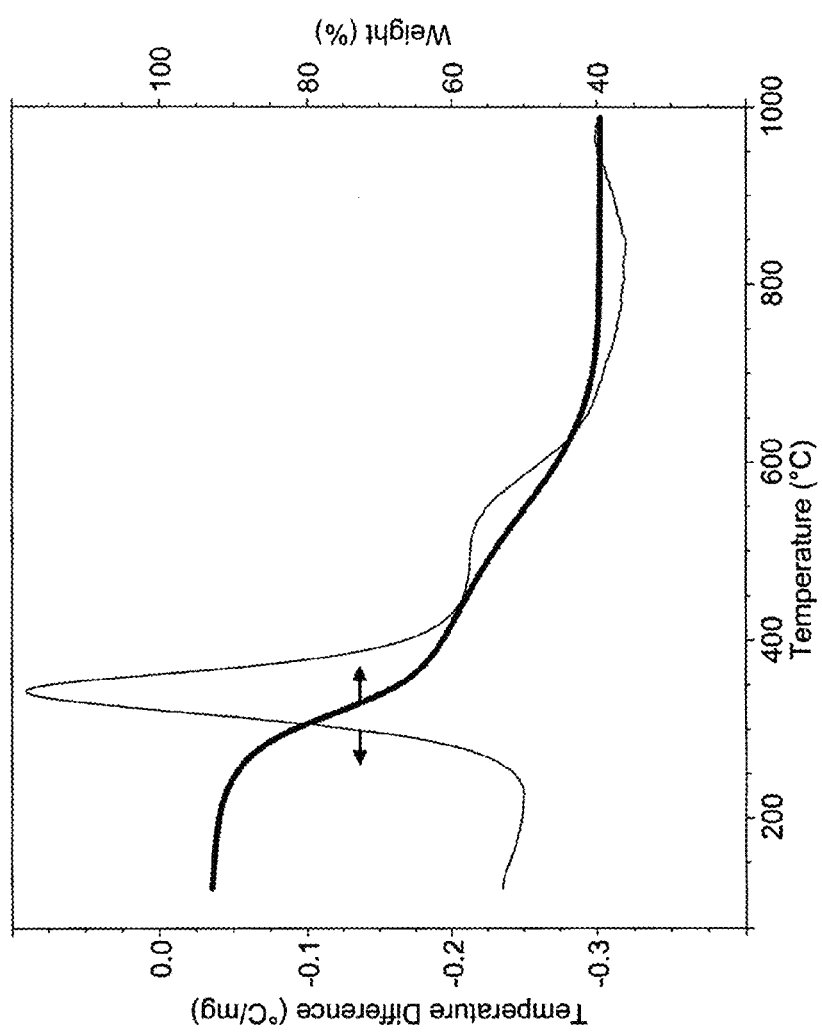
FIG. 19 shows representative TGA and DTA profiles for ca. 7 mg CHO derived CSCs (ramp rate, 10° C./min).

As an example of the present invention, chemically fixed mammalian cells were incubated in dilute, silicic acid solutions as shown in FIG. 1. FIG. 1a is a schematic illustration of the process of cell silicification. In a typical experiment, cells plated onto glass substrates were fixed using 2-4% fixative (formaldehyde and glutaraldehyde produced qualitatively similar results) for at least 10 minutes. Cells were rinsed and immersed overnight (~16 hrs) in a solution of 100 mM silicic acid at pH 3 and ~40° C. resulting in a composite comprising primarily silicon, oxygen, and carbon (cell/silica composites, CSCs). Calcination was performed in air at 550 to 600° C. for 3-4 hours which eliminated the majority of organics, as shown in FIG. 19. FIG. 1b shows brightfield images of the identical grouping of differentiated AsPC-1 pancreatic carcinoma cells throughout the process shown in FIG. 1a: live, after fixation, silicification and drying, and calcination. Insets show representative EDS spectra of cells at the various stages. Structural features and dimensions were observed at each stage of the process to be nearly identical to those of the parent (cell) templates albeit with some minor cracking observed, from SEM images of substrate bound, calcined CSCs, as shown in FIG. 1d. Additionally, features of hydrated living cells that were virtually transparent under brightfield microscopy appeared sharply resolved in calcined CSCs (e.g., the calcined sample imaged in FIG. 1c) due to the increase in refractive index contrast.

Figure 2:
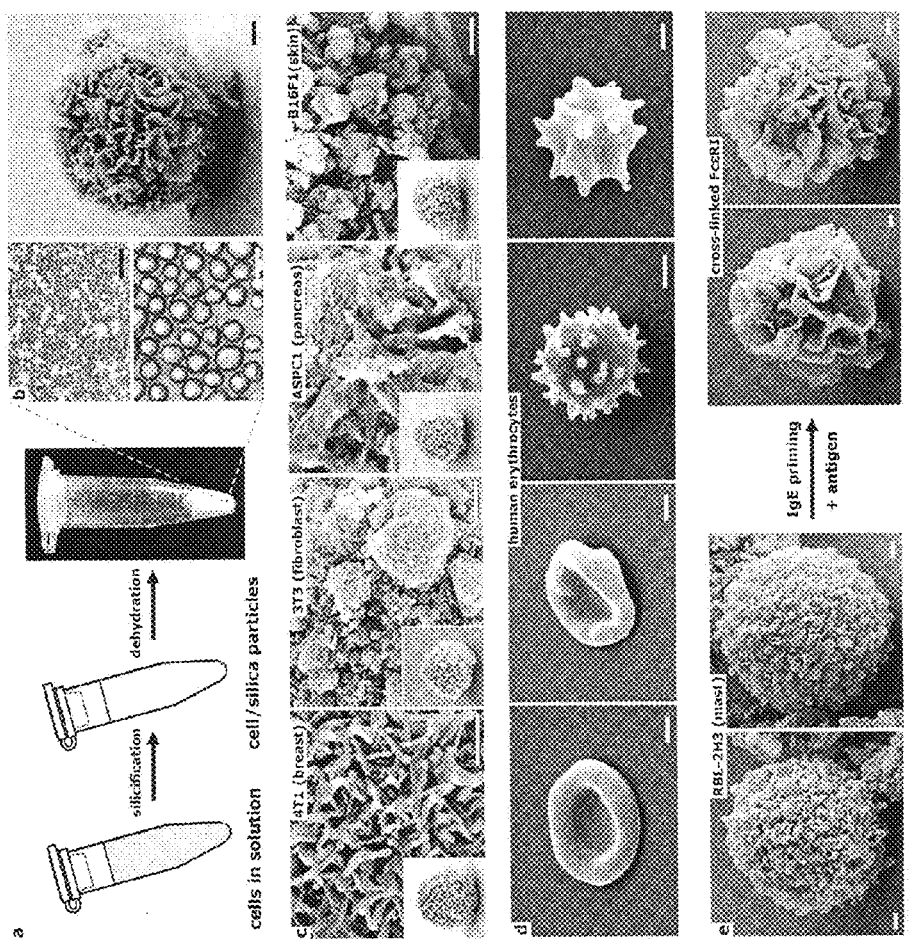
FIG. 2 shows CSC particles derived from cell suspensions. Provided are (a) a schematic illustration the formation of CSC particles; and (b) an image of a dry powder comprised of monodisperse CSC particles resulting from silicification, as for adherent cells, and dehydration. The large panel shows a close-up SEM of a 4T1 templated CSC displaying a ruffled external surface. Provided are (c) close-up SEMs of CSC particles derived from a variety of tissues. Insets show the whole particle. Provided are (d) calcined CSCs templated from human erythrocytes showing normal to increasingly abnormal/crenate morphology resulting from increasing levels of osmotic stress (left to right). Also provided are (e) calcined CSCs derived from RBL-2H3 cells before (left panels) and after (right panels) IgE crosslinking. Scale bars for (c)-(e): 1 μm.
Figure 3:
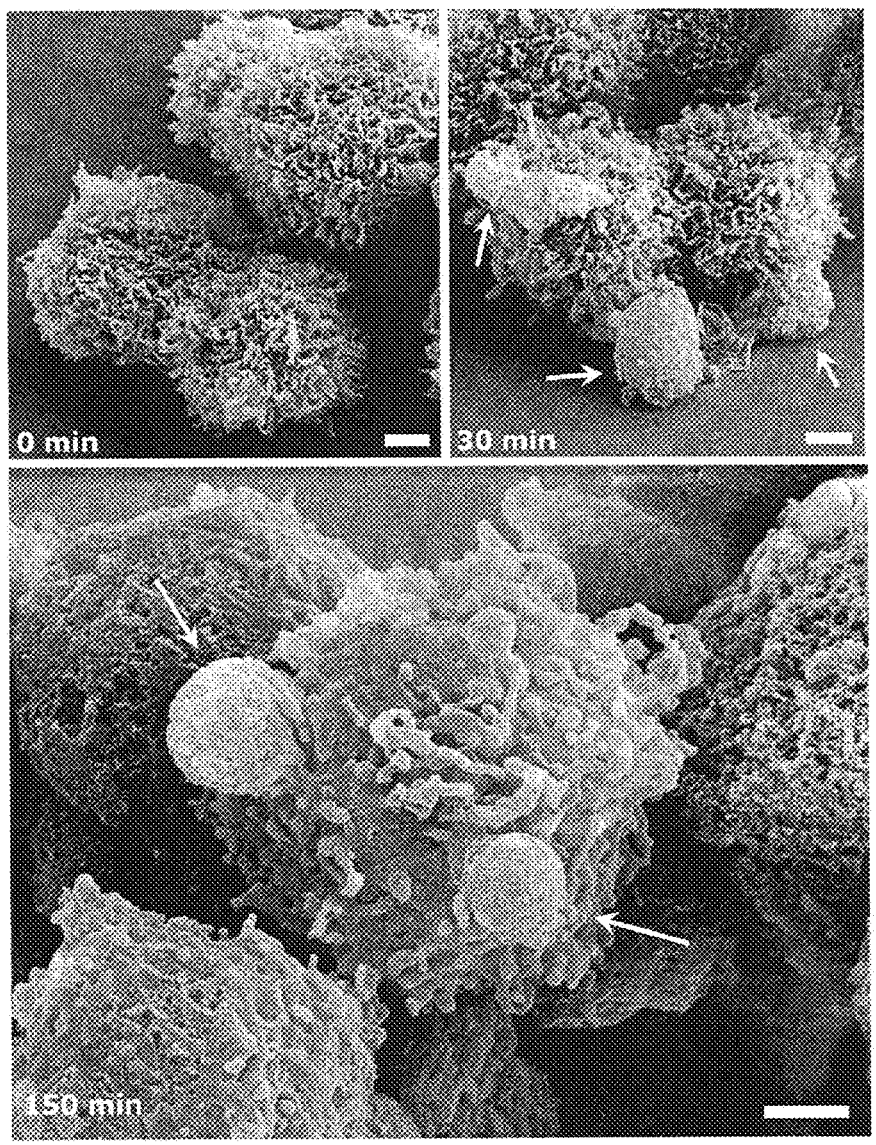
FIG. 3 are SEM images of clusters of calcined (500° C., 3 hrs) silica replicas templated from 4T1 cells incubated for 0, 30 and 150 minutes in 5 μm doxorubicin to induce apoptosis. Scale bars: 2 μm.

Cellular and sub-cellular morphology is dependent on genetic and environmental factors and therefore can be highly malleable and responsive to, for instance, physical interactions with a substrate. As shown in FIG. 1, the morphology of cells differentiated on a substrate can be faithfully captured in silica. Procedures were also developed under conditions that give rise to more physically homogenous CSC particles with high throughput. FIG. 2a is a schematic illustration of the formation of monodisperse CSC particles. Similar to silicification as for adherent cells, CSC particles were derived by incubating cell suspensions in TMOS on a shaker. For rinsing and drying, cells were pelleted and redispersed sequentially in rinse solutions (described above) and finally air-dried overnight from 100% methanol. Dehydration results in a dry powder comprised of monodisperse CSC particles. As shown in FIG. 2b, cells fixed and silicified under suspension conditions resulted in a population of essentially monodisperse composite microparticles (e.g., average diameter of 4T1 derived CSCs shown was 8.9 µm±1.4) with complex surface features. The large panel in FIG. 2b shows a closeup SEM of a 4T1 templated CSC displaying a ruffled external surface. For fast growing CHO cells (doubling time ~12 hours) a standard 225 $cm^2$ flask of adherent cells at 80% confluency (~2.0×$10^7$ cells) yielded ~10-20 mgs dry weight of CSCs, providing a means to rapidly produce gram scale quantities from cell lines such as CHO using large capacity bioreactors. See J. N. Warnock and M. Al-Rubeai, *Biotechnol Appl Biochem* 45, 1 (2006); and Z. Xing et al., *Biotechnol Bioeng* 103(4), 733 (2009). This procedure was tested on cultured cells derived from a variety of tissues. Similar particle sizes within a given clonal cell line were observed but with widely differing surface morphologies both within and across the cell lines examined. FIG. 2c shows close-up SEMs of CSC particles derived from a variety of tissues. Insets show the whole particle. Membrane ruffles, filaments, blebs, clusters, and smooth surfaces—common features of cell membrane dynamics—are captured in CSCs and calcined CSCs with high fidelity. Importantly, surface features of silica replicas can be directly modified by inducing cell behaviors, such as apoptosis, and surface ruffling prior to silicification. In particular, FIG. 3 shows SEM images of clusters of calcined (500° C., 3 hrs) silica replicas templated from 4T1 cells incubated in 5 µm doxorubicin to induce apoptosis. The arrows denote apoptotic blebs and flementous surface structures that appear to degrade over the 150 min incubation. FIG. 2d shows calcined CSCs templated from human erythrocytes showing normal to increasingly abnormal/crenate morphology resulting from increasing levels of osmotic stress (left to right). FIG. 2e shows RBL-2H3 templated CSCs following calcination which display the predicted grainy to ruffled membrane surface transformation accompanying surface receptor crosslinking. See B. S. Wilson et al., *Mol Biol Cell* 9(6), 1465 (1998).

Figure 4:
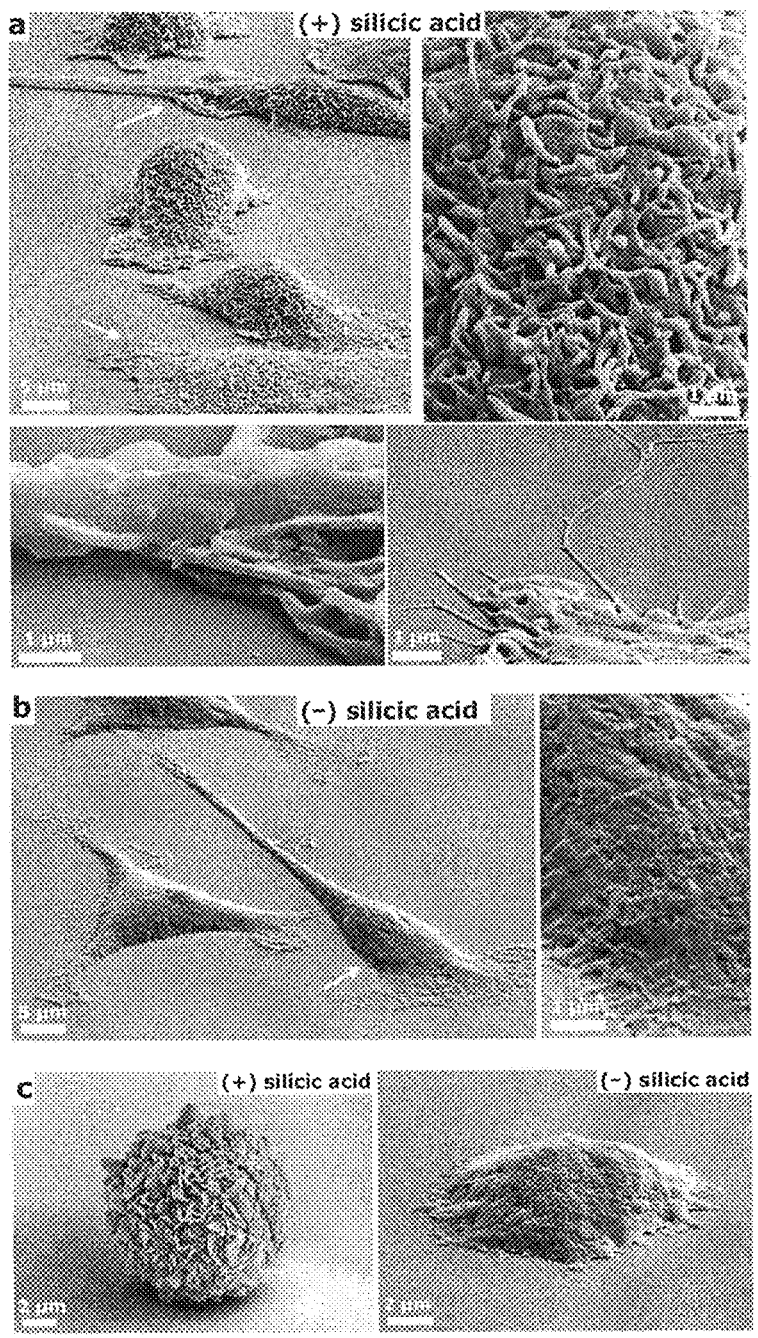
FIG. 4 are SEM images. Provided are (a) an SEM of AsPC-1 templated CSC features (indicated by (+) silicic acid); and (b) an SEM of cells fixed and dehydrated using standard procedures (indicated by (−) silicic acid). Magnified features are indicated by arrows. Also provided are (c) SEM images of SK-OV-3 suspension cultured cells dried against a substrate with (+) and without (−) silicic acid treatment.
Figure 5:
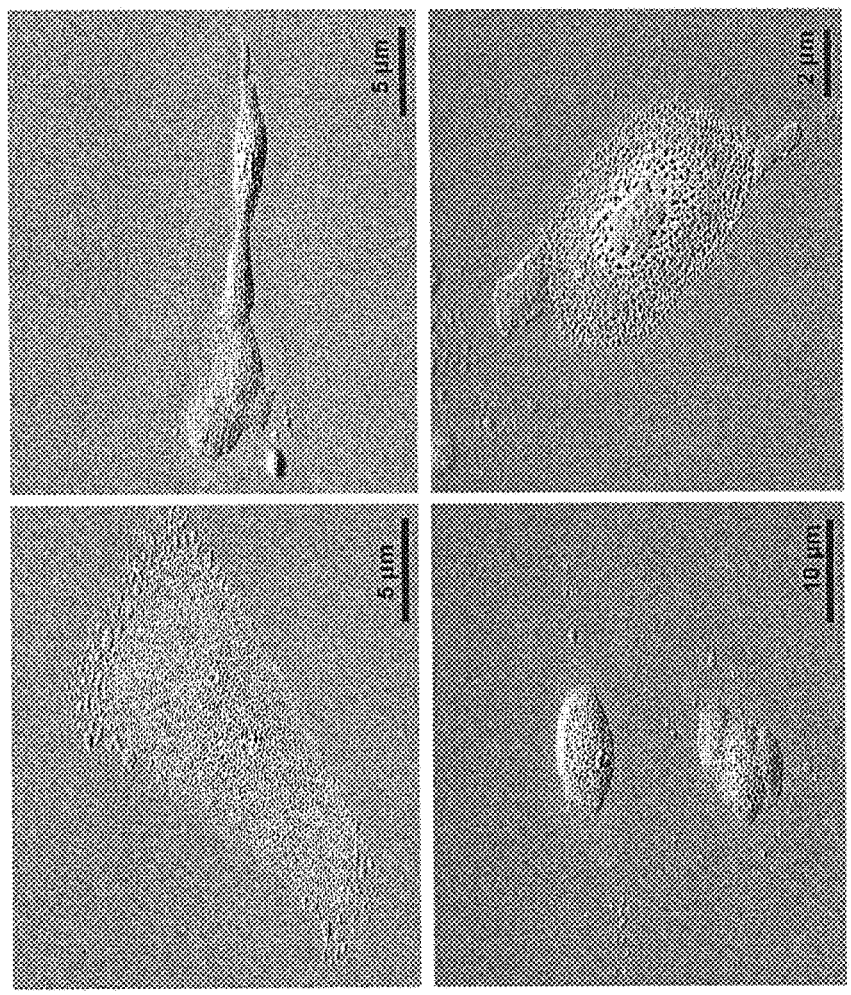
FIG. 5 shows SEM images of calcination of fixed ASPC1 cells in the absence of silicic acid treatment.

FIG. 4a shows an SEM of AsPC-1 templated CSC features prepared according to the present invention. FIG. 4b shows cells fixed and dehydrated using standard procedures. Magnified features are indicated by arrows in FIGS. 4a and 4b. FIG. 4c shows SEM images of SK-OV-3 suspension cultured cells dried against a substrate with and without silicic acid treatment. External features of CSCs in FIG. 4a show more defined and detailed surface structures compared to the identical cell line prepared using the well-established bench top electron microscopy preparation procedures (i.e., no supercritical drying or rapid freezing) of fixation followed by careful dehydration in increasing concentrations of ethanol and drying from hexamethyldisilazane HMDS, shown in FIG. 4b, a procedure shown to provide identical feature preservation as critical point drying. See F. Braet et al., *J Microsc* 186, 84 (1997); and D. F. Bray et al., *Microsc Res Tech* 26(6), 489 (1993). Note that silicification can alter the size of nanoscale cellular features in comparison to drying from HMDS. Suspension cells silicified in solution showed particularly dramatic differences compared to non-silicified cells. As shown in FIG. 4c, CSC particles dried in contact with a substrate (and even calcined) were resistant to deformation, remaining stiff and spherical, whereas the parent fixed cells deformed significantly with loss of surface features during drying, and of course were completely obliterated upon calcination in the absence of silicic acid treatment, as shown in FIG. 5. Thus, silicification acts to mechanically stabilize the cellular architecture during drying and particularly during calcination, by forming a continuous, mechanically connected interpenetrating network throughout the 'cell hydrogel', analogous to results from protein-templated silica hydrogels. See C. Y. Khripin et al., *ACS Nano* 5, 1401 (2011). The present invention can therefore provide a simple alternative to common methods for specimen preparation/preservation that does not require extensive optimization, expertise, or specialized equipment (e.g., critical point dryer), and particularly when tolerance to extreme environments (e.g., temperature) is required.

Figure 6:
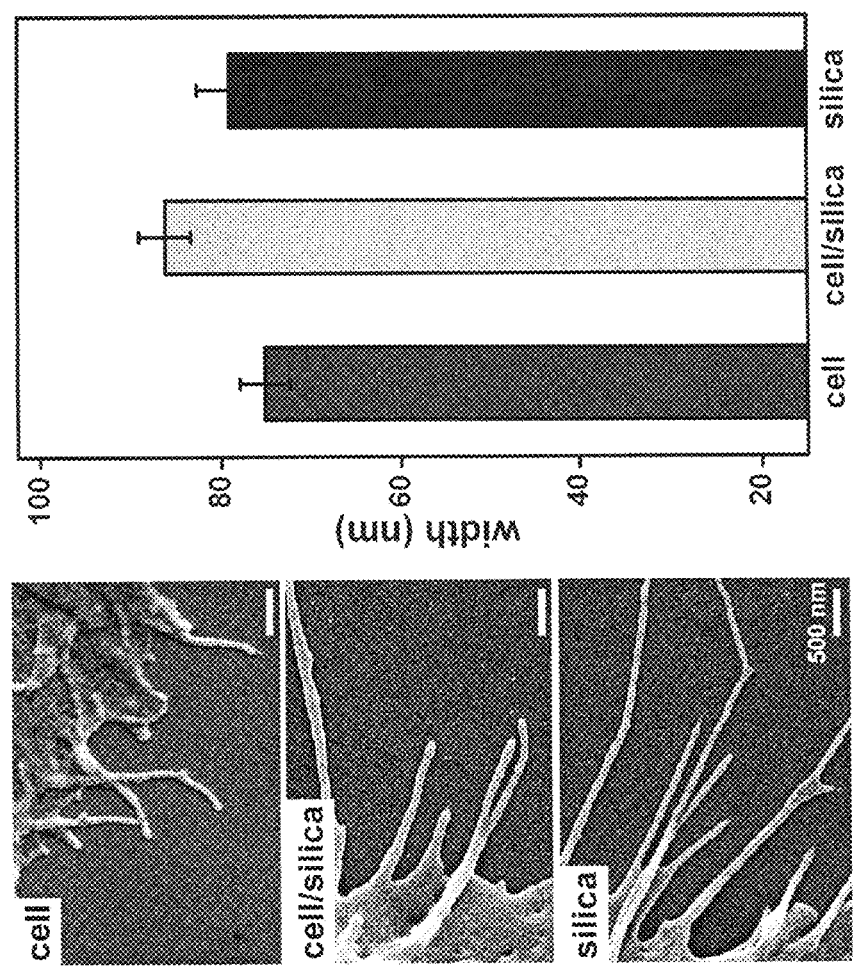
FIG. 6 shows an SEM analysis of filopodia mean width of fixed cells (75 nm), cell/silica composites (86 nm), and silica (79 nm) derived from substrate-bound differentiated AsPC-1 cells. Error bars indicate the standard error of the mean.

FIG. 6 shows an SEM analysis of filopodia mean width of fixed cells (75 nm), cell/silica composites (86 nm), and silica (79 nm) derived from substrate-bound differentiated AsPC-1 cells, indicating a significant difference in mean width (at 0.05 level using overall ANOVA, n >15 per sample). The "cell" sample was prepared using EtOH:HMDS sample preparation. Error bars indicate the standard error of the mean. SEM comparisons of substrate bound differentiated AsPC-1 cells indicates an increase in the size of nano-scale cellular features throughout the procedure (~10 nm increase in width of CSC filopodia outgrowths versus non-silicified cells), which is attributed to silica deposition.

Figure 7:
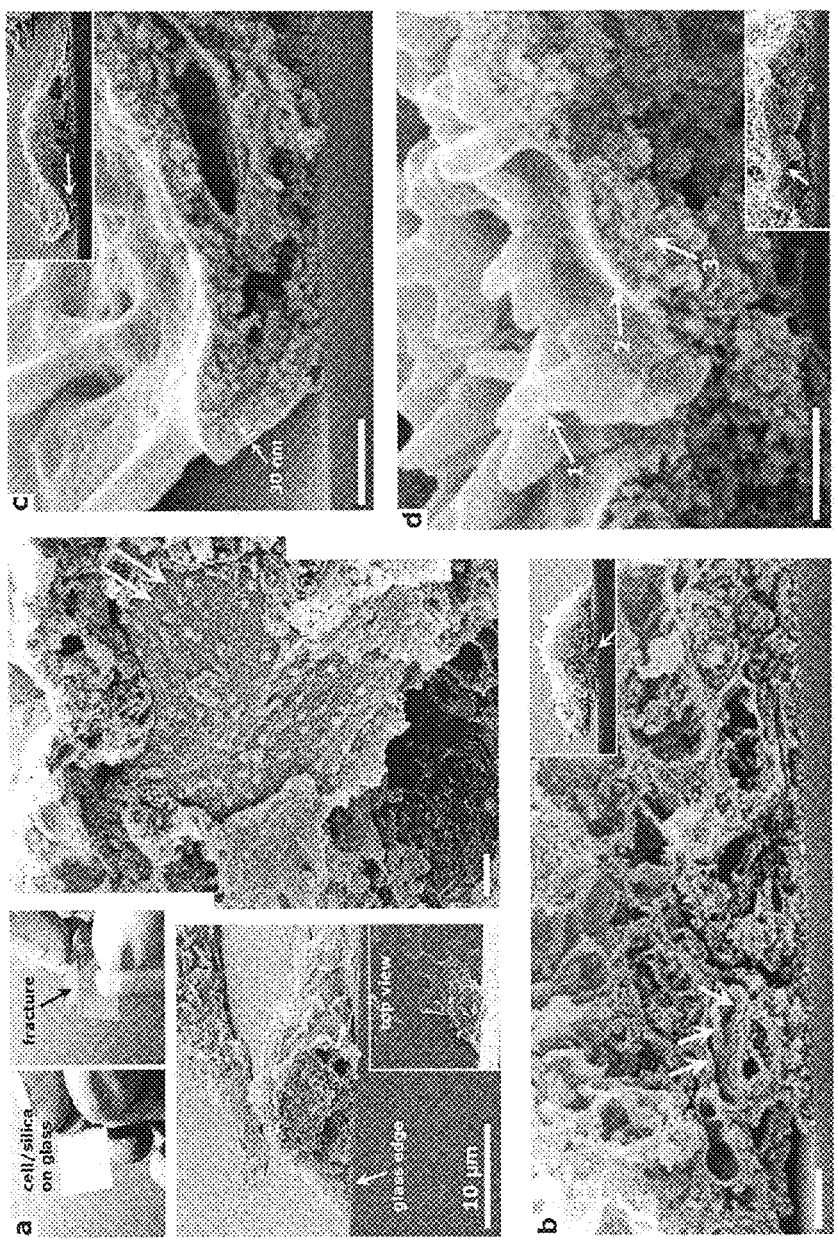
FIG. 7 shows cross-sectional SEM imaging of CSCs enabled by a simple fracture technique. Provided is (a) an SEM image of the fracture of CSCs on a coverslip provides clean sectioning to reveal intracellular features using SEM. The right panel is a close up view of the sectioned cell. Arrows indicate nuclear pore complexes. Provided are (b) an SEM section of a CSC showing multilayer, endoplasmic reticulum-like structures, indicated by arrows; (c) an SEM of a calcined CSC sectioned on glass showing a 30 nm membrane templated silica structure; and (d) an SEM of Filopodia-templated upright protrusions that (1) are encased in a smooth silica membrane (2) overlying roughened, particle-based features (3) in a calcined and sectioned CSC. Arrows in (b)-(d) insets point to the area of magnification. All scale bars: 500 nm.

In order to examine the internal features of CSCs in greater detail, AsPC-1 cells were plated onto glass substrates, silicified, and dried. FIG. 7 shows cross-sectional imaging of CSCs enabled by a simple fracture technique. Glass substrates were scored on the surface opposite the cells and fractured. Because of the brittle fracture characteristics of the CSCs, cells lying across the fracture edge were often cleanly sectioned, allowing cross-sectional analysis using scanning electron microscopy. FIG. 7a shows a sectioned cell revealing intra-cellular structures such as the nuclear membrane, indicated by 100 nm diameter ring-like features (presumably nuclear pore complexes). The right panel is a close up view of the sectioned cell. Arrows indicate nuclear pore complexes. FIG. 7b is an SEM section of a CSC showing multilayer, endoplasmic reticulum-like structures (arrows). FIG. 7c is an SEM of a calcined CSC sectioned on glass shows a 30 nm membrane templated silica structure. FIG. 7d shows Filopodia-templated upright protrusions (1) are encased in a smooth silica membrane (2) overlying roughened, particle-based features (3) in a calcined and sectioned CSC. The arrows in the insets of FIGS. 7b-7d point to the area of magnification. Comparison of fractured CSCs (e.g., FIGS. 7a and 7b) and fractured calcined CSCs (FIGS. 7c and 7d) showed no obvious difference in size or shape of internal features after calcination.

Figure 8:
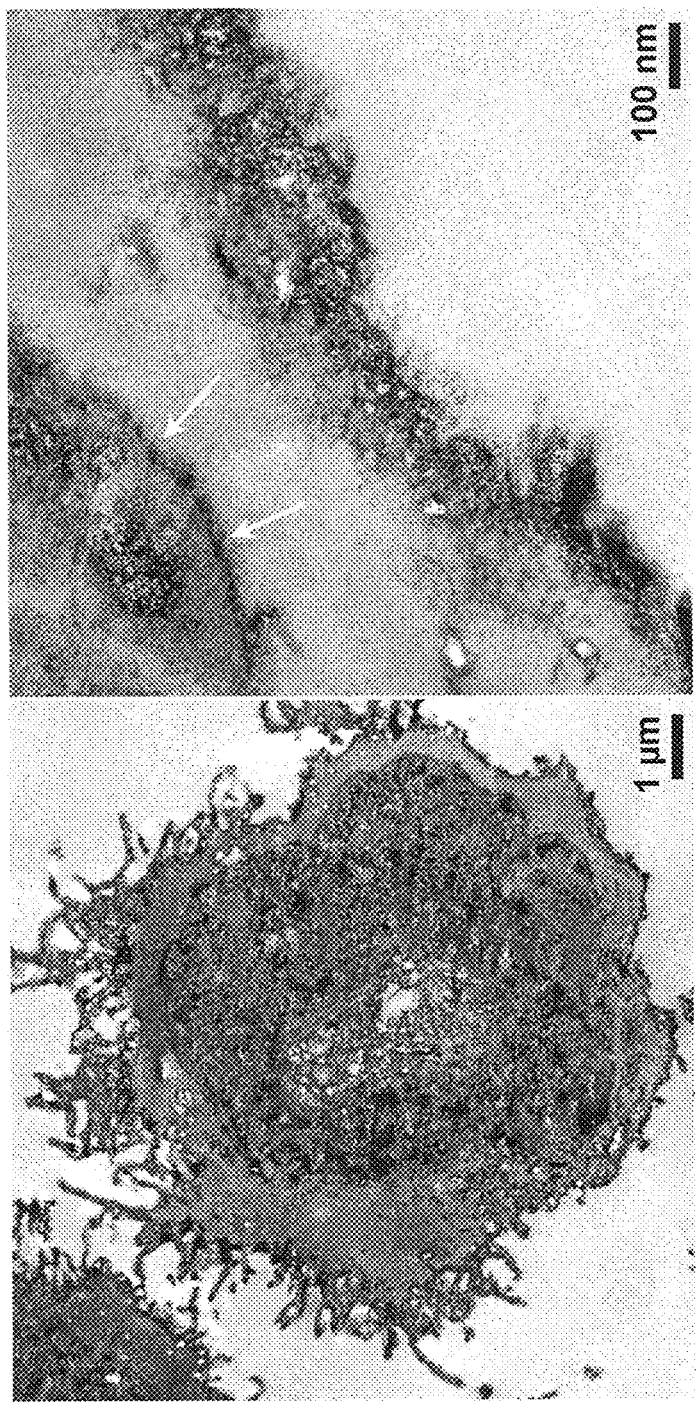
FIG. 8 shows unstained TEM cross section of 4T1 derived CSC showing high contrast at the outer and nuclear membrane (arrows) attributed to areas of high silica concentration.

FIG. 8 shows unstained TEM cross section of 4T1 derived CSC showing high contrast at the outer and nuclear membrane (arrows) attributed to areas of high silica concentration. Examining calcined structures, such as those in FIGS. 7c and 7d, as well as TEM cross-sectional images of CSC particles, such as those in FIG. 8, a conformal silica coating of ca. 30 nm thick is apparent, elaborated around filopodia-like features (shown in FIG. 7d) and encasing the intracellular-templated structures and void spaces. In a eukaryotic cell, the membrane is defined by the phospholipid bilayer anchored to the cell cortex via membrane bound proteins.

Figure 9:
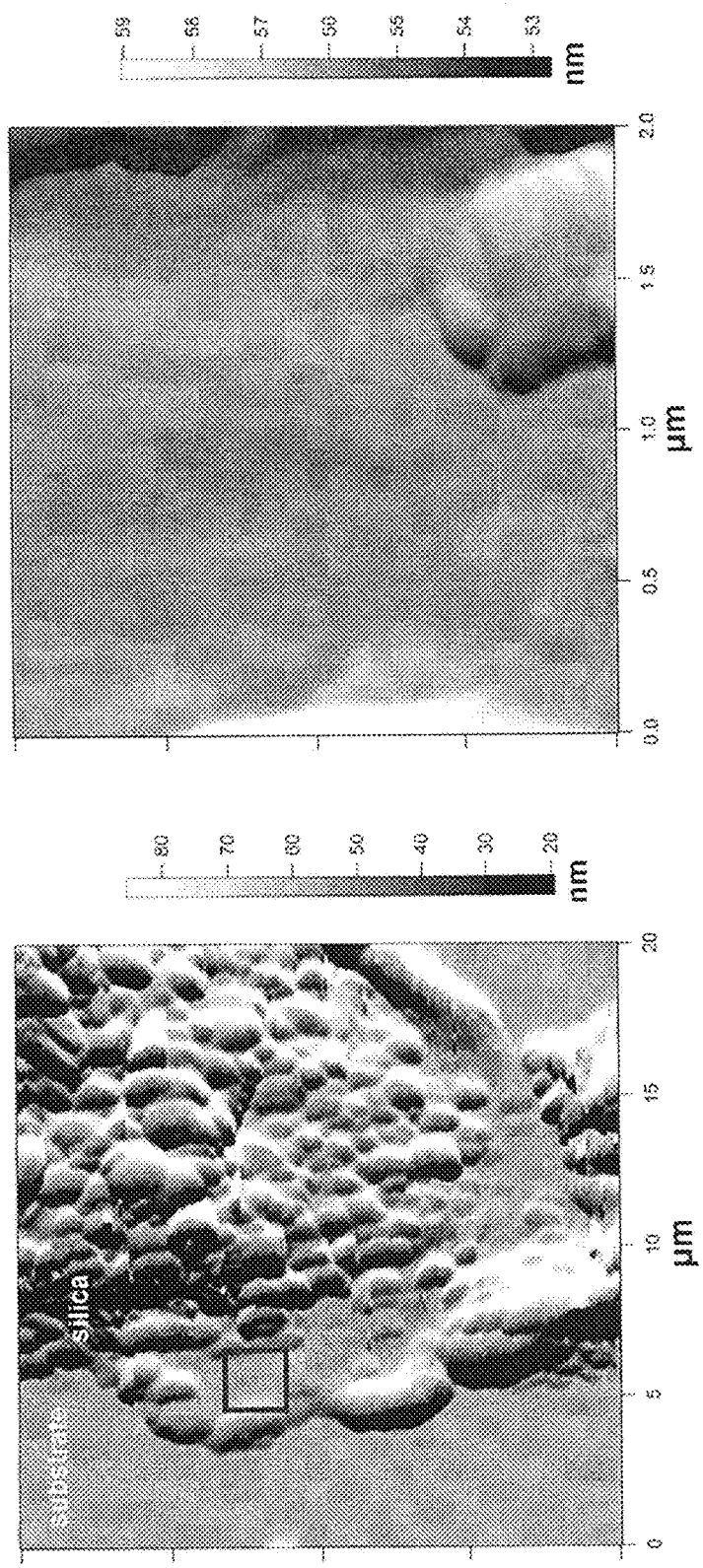
FIG. 9 shows atomic force microscopy (AFM) images of the external surface of a calcined CSC derived from ASPC-1 cells.

The cortex is composed of fibrous proteins such as spectrin and actin, forming a meshwork that provides mechanical strength to the membrane. High resolution atomic force microscopy (AFM) imaging of relatively flat regions of calcined external surfaces were featureless at ~2 nm resolution indicating the absence of a primary feature or particle size. FIG. 9 shows AFM images of the external surface of a calcined CSC derived from ASPC-1 cells. Analysis of the height image (right panel; scanned area of the box in the left panel) was used to measure surface roughness (standard deviation, $\sigma=1$ nm) within error attributed to the tip radius (<2 nm). Similar observations were made in AFM studies of select diatom cell surfaces. See M. Hildebrand and M. J. Doktycz, *Pflugers Arch* 456, 127 (2008). In comparison, silica templated by single component protein hydrogel scaffolds was observed to be granular with a primary feature size of ~16 nm. See C. Y. Khripin et al., *ACS Nano* 5, 1401 (2011).

Figure 10:
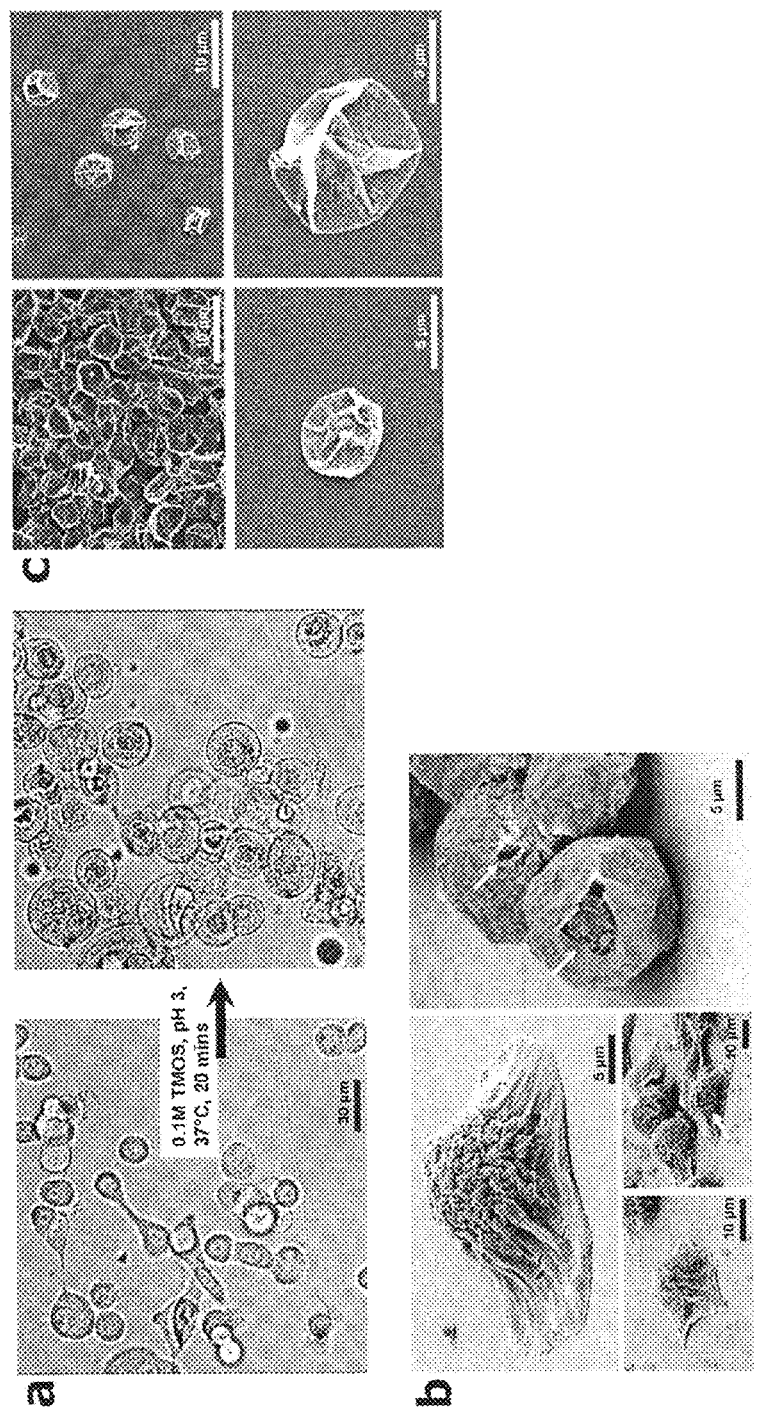
FIG. 10 shows light microscopy and SEM images. Provided are (a) an image of silicification of cells (AsPC-1) without chemical fixation; and (b) an SEM of calcined samples (AsPC-1, left panels; 4T1-particles, right panel) of unfixed cells. Arrows indicate areas of membrane rupture. Also provided are (c) images showing silicification of fixed erythrocytes induces cell lyses resulting in silica templated by erythrocyte membranes following calcination.

A series of experiments were conducted to understand the mechanism of cell silicification. First, cells subjected to silicification conditions without fixation were observed to swell significantly, as a result of hypotonic stress, but nonetheless formed CSCs (albeit with drastic differences in morphology due to membrane swelling and other stresses incurred during silicic acid incubation. Therefore, fixation can enable preservation of shape in the natural state, but is not required for all applications. FIG. 10a is an image of silicification of cells (AsPC-1) without chemical fixation, resulting in cell swelling indicative of hypo-osmotic cellular stress. FIG. 10b is an SEM of calcined samples (AsPC-1, left panels; 4T1-particles, right panel) showing the resultant cell templated silica with altered morphology. The light arrows indicate areas of membrane rupture. Erythrocytes are particularly sensitive to osmolarity and were found to lyse in the silicic acid solution when fixed for short time scales. FIG. 10c shows that silicification of short time fixed erythrocytes induces cell lyses resulting in silica templated by erythrocyte membranes following calcination. Through a modified fixation process and use of an osmotically balanced silicic acid solution (addition of 0.9% NaCl), CSCs and calcined erythrocytes silica replicas were achieved that faithfully replicated the parent cell morphology shown in FIG. 2d.

Figure 11:
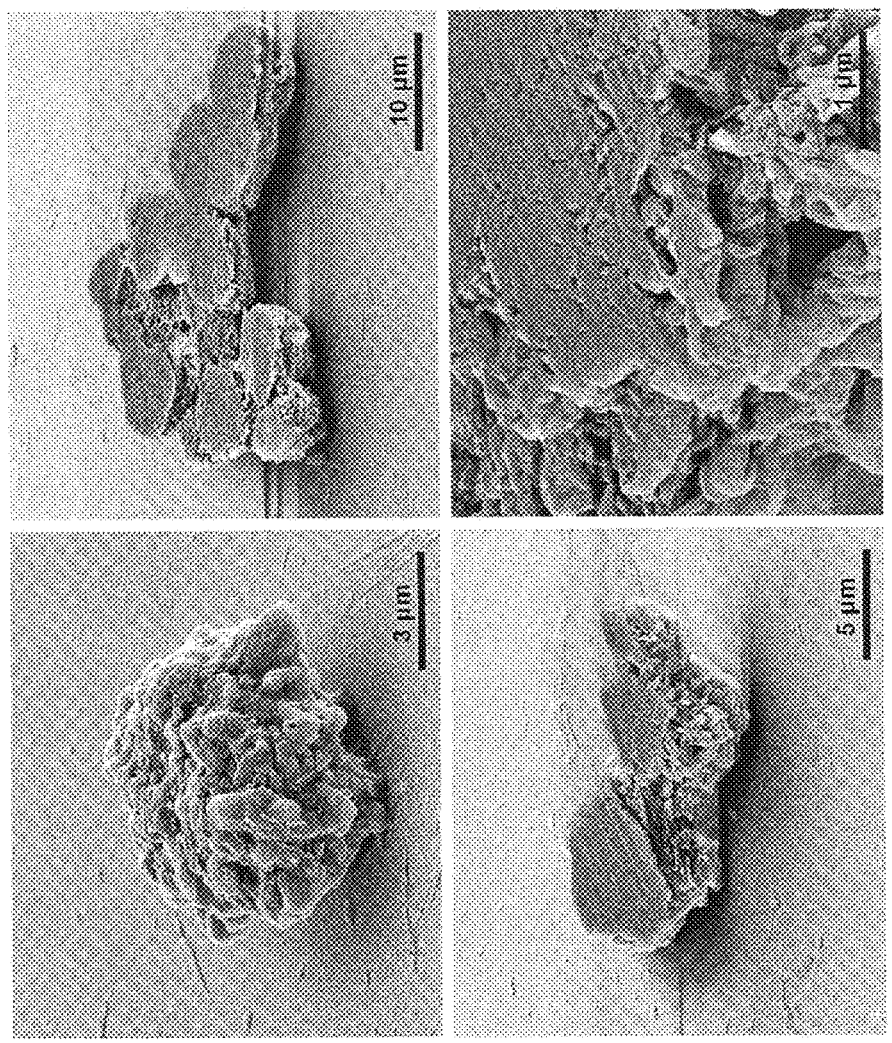
FIG. 11 is SEMs of 4T1 cells incubated in 0.5% Triton X-100 prior to silicification, resulting in CSCs with altered surface morphologies and flattened regions.
Figure 12:
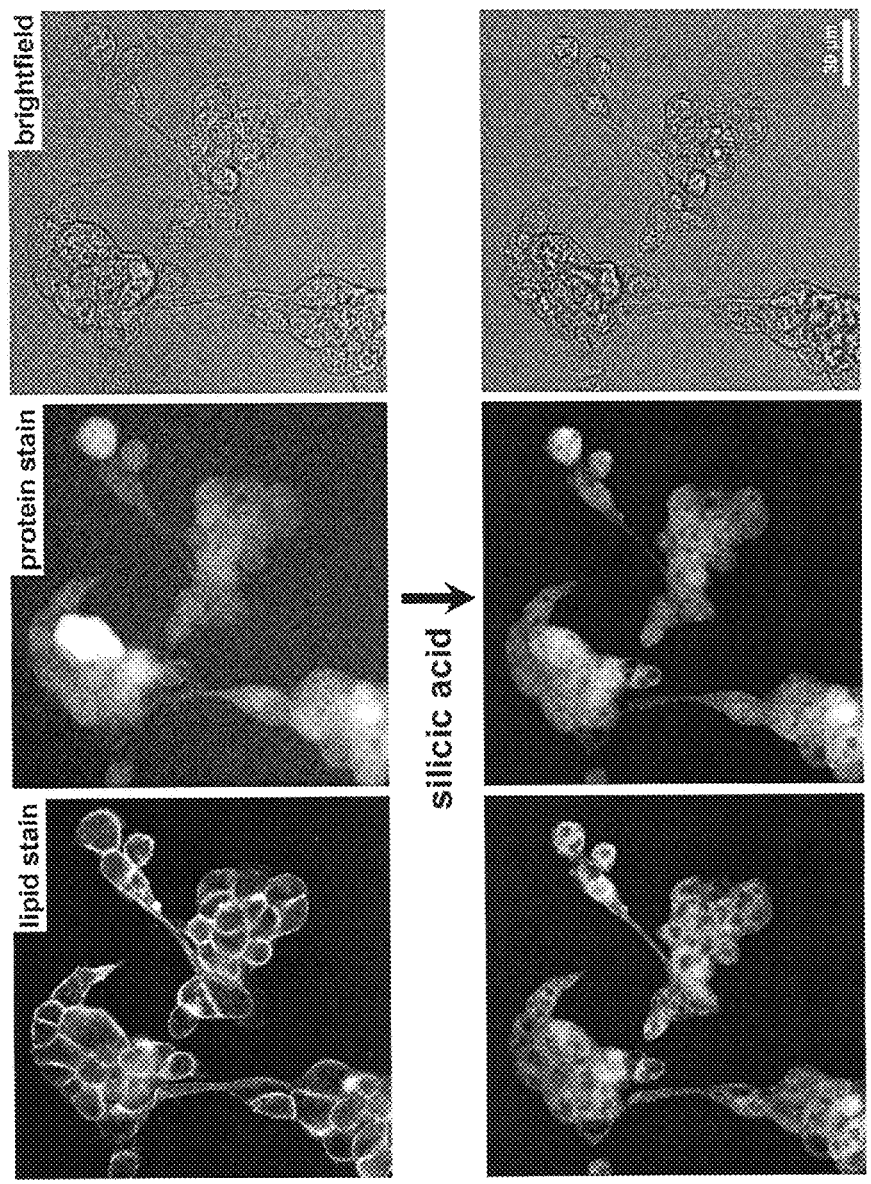
FIG. 12 shows images of ASPC1 cells fluorescently stained for outer membrane (CellMask™ Orange) and cytoplasmic proteins (CellTracker™ Green) before silicification (top panels), showing loss of membrane dye localization while the protein dye remained stationary.

As shown in FIG. 11, complete solubilization of the membrane of fixed cells using a mild detergent (0.5% Triton X-100) prior to silicification resulted in CSCs with deformed features, most likely incurred as a result of settling against the reaction tube surface. However, staining of the outer lipid membrane and intracellular proteins followed by silicification showed some de-localization of lipid following incubation in the silicic acid solution (also, confirmed by post-staining CSCs using a lipid-associating dye) while the protein dye remained stationary. FIG. 12 shows ASPC1 cells fluorescently stained for outer membrane (CellMask™ Orange) and cytoplasmic proteins (CellTracker™ Green) before silicification (top panels) showing loss of membrane dye localization while the protein dye remained stationary. Membrane staining of cells following silicification produced qualitatively similar results. Triton X-100 is not expected to disrupt the cortical layer or other cytoskeletal constituents, or denature most proteins at this concentration. Taken together, these results indicate that the whole membrane complex (lipid bilayer+cortex) is necessary to maintain the mechanical integrity of CSC surfaces, but that a portion of the lipid component is gradually displaced during silica deposition.

Figure 13:
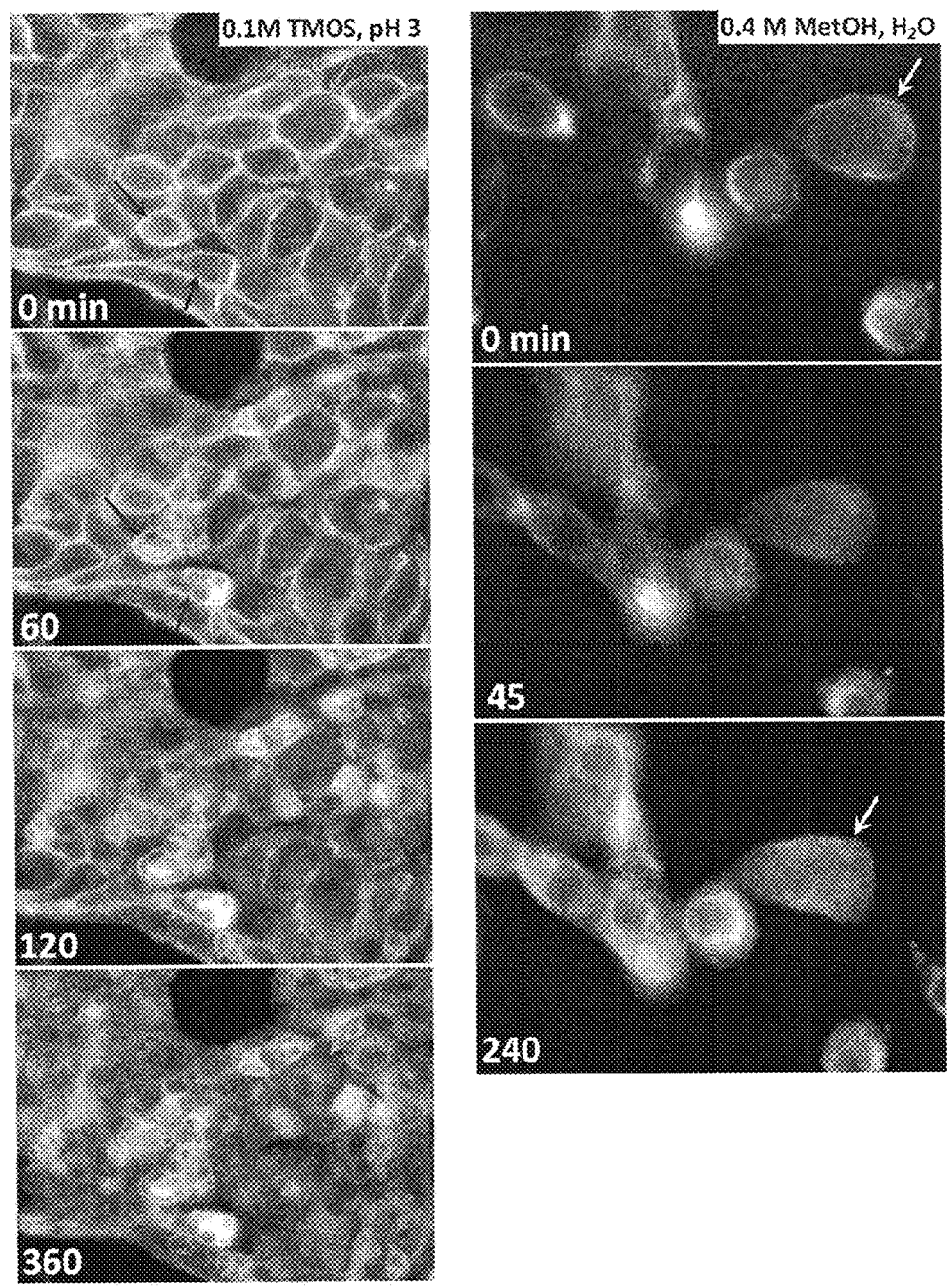
FIG. 13 shows time lapse imaging of fixed AsPC-1 cells fluorescently stained for outer membrane (CellMask™ Orange) under silicification conditions (left panels) and methanol (right panels) both at 37° C. Scale bars: 10 μm.

Indeed, time-lapse imaging of a lipid membrane dye indicates that the presence of dilute methanol (hydrolyis product of TMOS) in the silicification solution provides relatively slow and mild permeabilization of cell membranes (compared to methods used for immunostaining, such as Triton and 100% methanol) that enables silica precursors to penetrate into the cell while maintaining the mechanical integrity of external cell features during silica deposition. FIG. 13 shows time lapse imaging of fixed AsPC-1 cells fluorescently stained for outer membrane (CellMask™ Orange) under silicification conditions (left panels) and methanol (right panels) both at 37° C. Delocalization of fluorescent dye from the cell exteriors with concurrent increase in interior fluorescence indicates that the timescale for membrane permeabilization varies from cell to cell, occurring over minutes to hours (arrows in left panels). Similar observations in 0.4 methanol (arrows in right panels) indicate membrane permeabilization is primarily due to incubation in methanol generated from the acid catalyzed hydrolysis of the silicic acid precursor TMOS.

Figure 14:
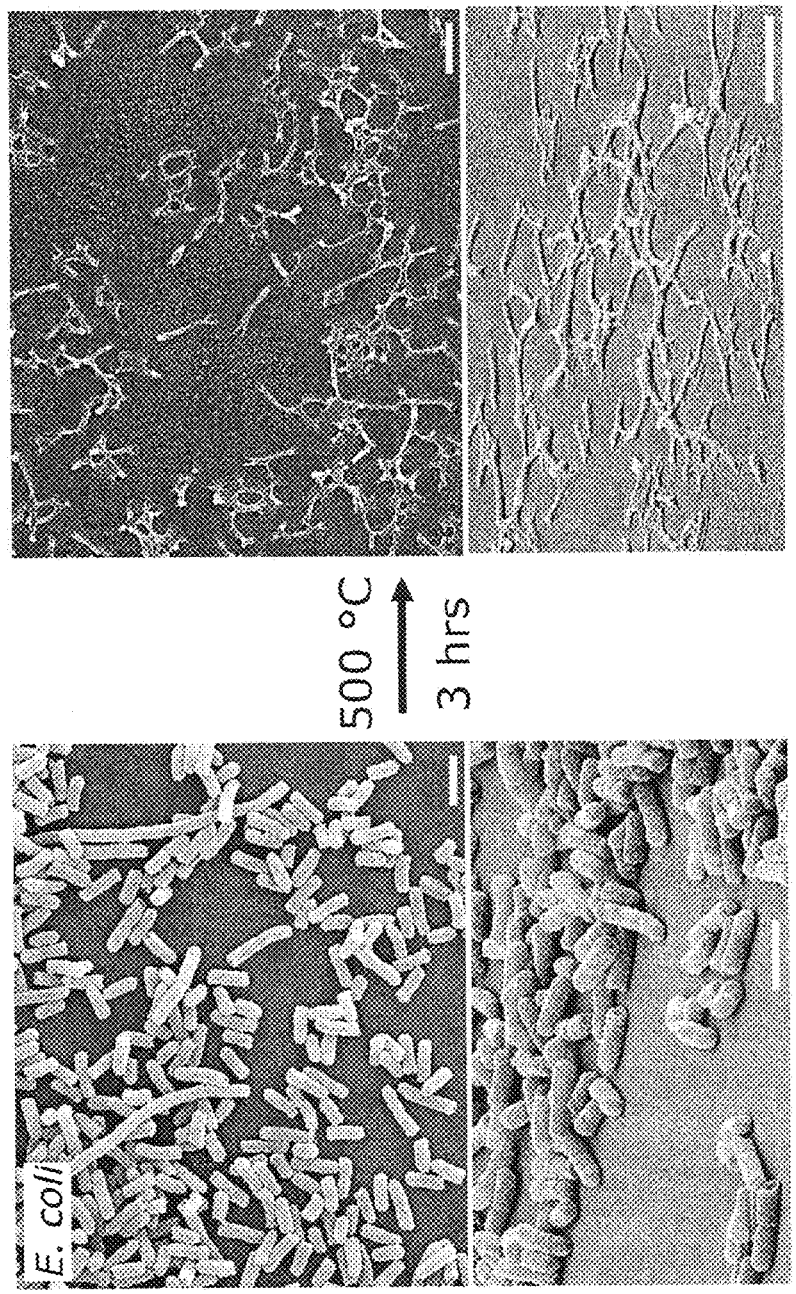
FIG. 14 shows SEM images of gram-negative bacterial cells (*E. coli*) silicified using identical conditions to those of mammalian cells (100 mM silicic acid, pH 3) indicates that following calcination (right panels) cellular-structure (left panels) is not stabilized (via intra-cellular silicification) and thus obliterated following calcination (right panels). Scale bars: 2 μm.

Additionally, CSCs derived from *E. coli* do not retain cellular structure following calcination which indicates incomplete silica templating, most likely as a consequence of inhibited intracellular penetration of silica precursors past the prokaryotic cell envelope. FIG. 14 shows SEM images of gram-negative bacterial cells (*E. coli*) silicified using identical conditions to those of mammalian cells (100 mM silicic acid, pH 3) indicates that following calcination (right panels) cellular-structure (left panels) is not stabilized (via intra-cellular silicification) and thus obliterated following calcination (right panels).

Figure 15:
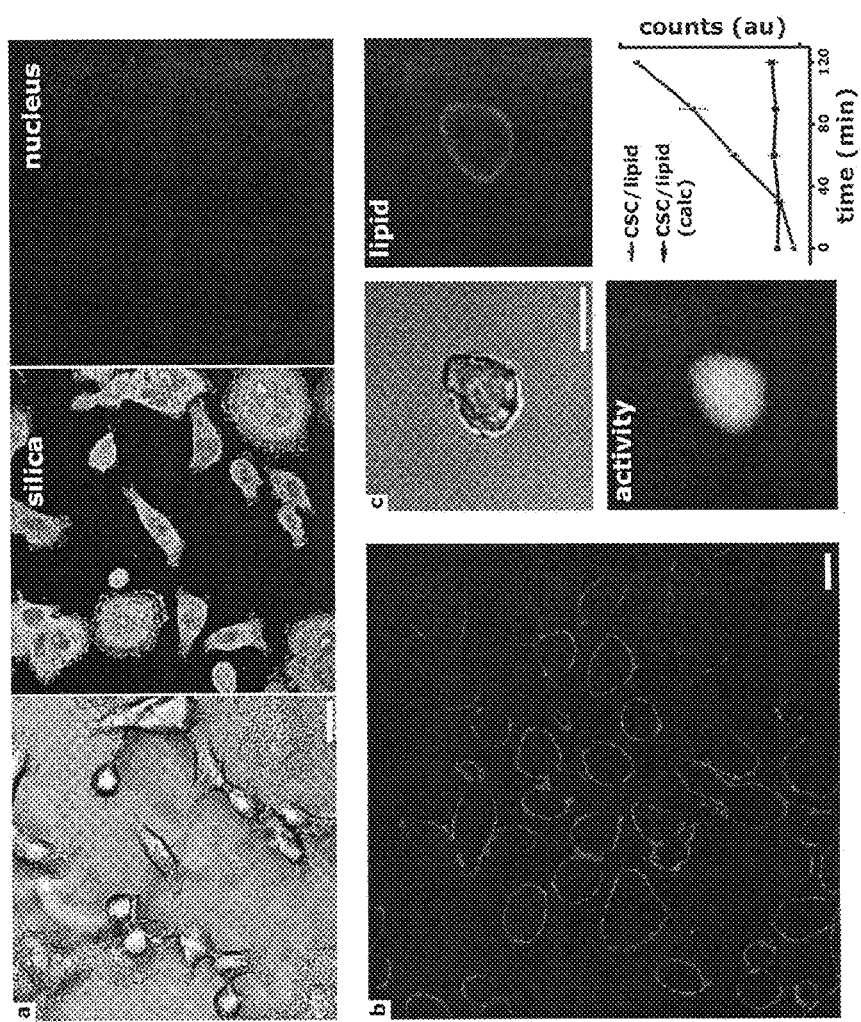
FIG. 15 shows images showing the distribution of silica in CSCs, nuclear staining, and lipid membrane reconstitution. Provided are (a) DIC and confocal fluorescence images of AsPC-1 templated CSCs, showing that silica is continuous throughout the cytoplasm and nucleus as indicated by PMPDO staining (middle panel). Right panel shows localization of DAPI nuclear stain. Also provided are (b) a confocal fluorescence image slice of substrate grown AsPC-1 CSCs showing surface localization of lipid and internal location of the nucleus; and (c) an image of CSC particles supporting lipid layers showing accumulation of esterase fluorogenic products, as indicated by the line labeled "CSC/lipid". The line labeled "CSC/lipid (calc)" shows activity of calcined CSCs supporting lipid bilayers. Error bars describe the standard deviation (n 5) of the maximum intensity value. Scale bars: 10 μm, (a) and (b); 5 μm, (c).
Figure 16:
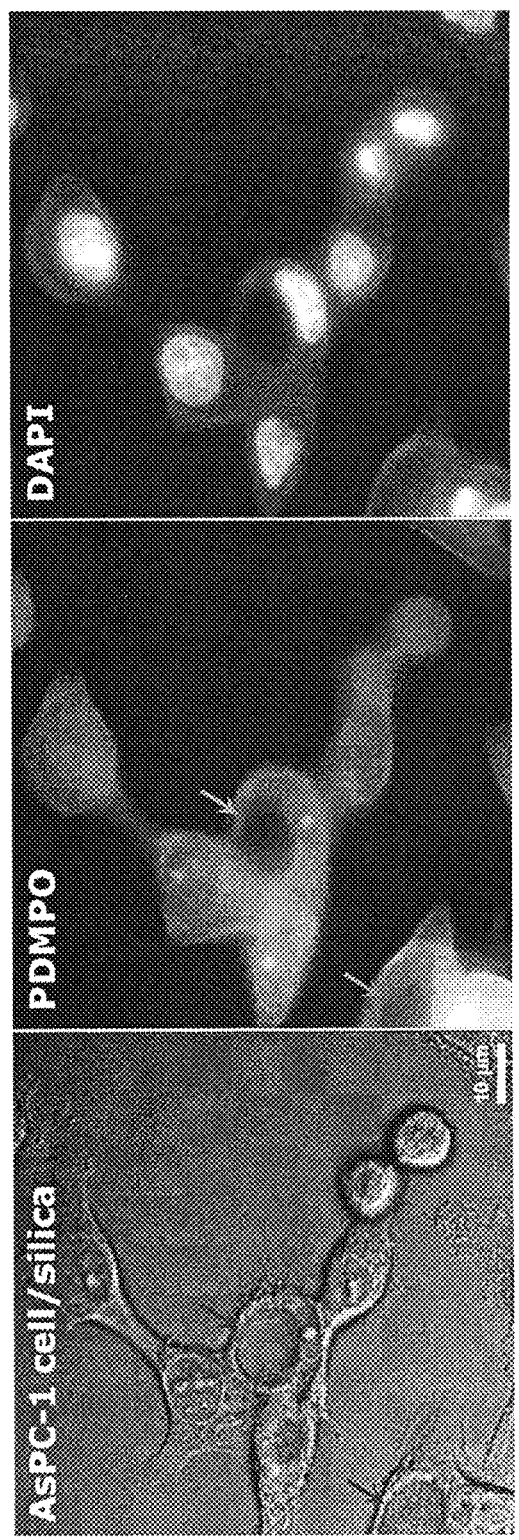
FIG. 16 is a brightfield (left panel) and epifluorescence (middle and right panels) images of AsPC-1 cell/silica composite particles.

Silica localization throughout the CSC was observed during silicification using PDMPO: ([2-(4-pyridyl)-5-((4-(2-dimethylaminoethylamino-carbamoyl)methoxy)phenyl)oxazole]), which has been shown to incorporate with silica as it condenses. See B. Tesson and M. Hildebrand, *PloS one* 5, e14300 (2010). FIG. 15 shows the distribution of silica in CSCs, nuclear staining, and lipid membrane reconstitution. FIG. 15a shows DIC and confocal fluorescence images of AsPC-1 templated CSCs showing that silica is continuous throughout the cytoplasm and nucleus following incubation for 16 hours, as indicated by PMPDO staining (middle panel). The right panel shows localization of DAPI nuclear stain. This indicates that although silica condensation is likely to occur over variable timescales at the (macro) molecular scale, it eventually infiltrates all discernible subcellular structures and organelles—with the notable exception of large, fluid filled vacuoles. FIG. 16 shows a brightfield (left panel) and epifluorescence (middle and right panels) images of AsPC-1 cell/silica shows silica localization (PDMPO panel) throughout the cellular interior—including the nucleus (DAPI panel)—with the noticeable exception of vacuole-type structures (arrows in left and middle panels). Further, the nuclear stain 4',6-diamidino-2-phenylindole (DAPI) is shown to localize exclusively within the nuclear region of CSCs with little background signal, as shown in FIGS. 15a and 15b. This indicates that when CSCs are incubated in an aqueous solution of the dye molecule, the DNA helical structure remains intact and molecularly accessible within the nucleus—despite silicification throughout the nuclear region.

Figure 17:
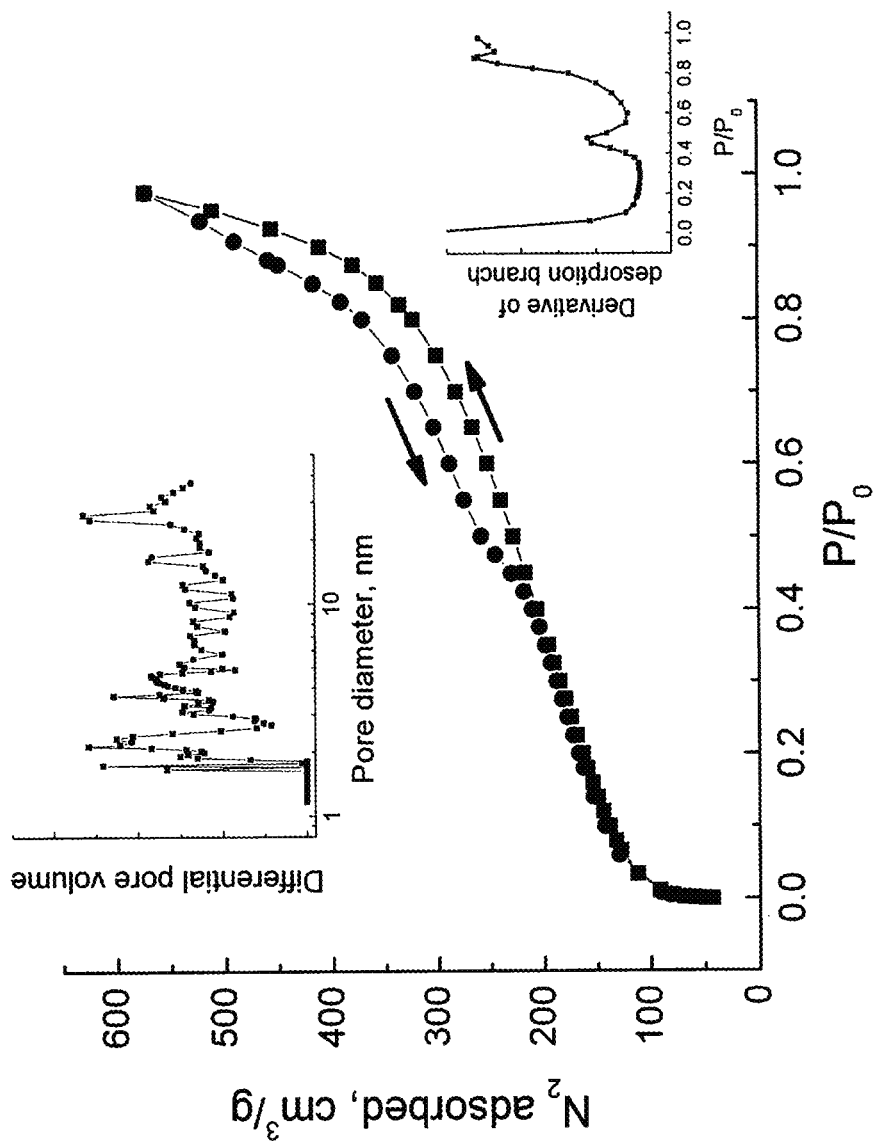
FIG. 17 shows a $N_2$ sorption isotherm of calcined CSCs templated from CHO cells.

$N_2$ sorption isotherms obtained from CHO-templated silica particles (representing a silica imprint of the internal and external cellular structure) indicated a BET surface area of ~365 $m^2/g$ and a broad range of pore dimensions, although with no appreciable microporosity. FIG. 17 shows a $N_2$ sorption isotherm of calcined CSCs templated from CHO cells. The lack of a distinct condensation step in the adsorption branch indicates a wide pore size distribution (PSD); a fit to the adsorption branch using a hybrid DFT model for cylindrical pores in silica (top inset) shows that the material contains a broad range of pore dimensions, although with no microporosity (pore size less than 2 nm). See M. Jaroniec et al., *A new method for the accurate pore size analysis of MCM-41 and other silica based mesoporous materials*, Fifth International Symposium on the Characterization of Porous Solids, COPS V, Heidelburg; Unger, K. K.; Kreysa, G.; Baselt, J. P., Eds. Elsevier: Heidelburg, pp 71-80 (1999). Because there is no plateau in the adsorption branch at high $P/P_0$, the total porosity for pores greater than ca. 40 nm cannot be determined from this isotherm. However, hysteresis in the desorption branch—likely due to a bottleneck structure within a pore network—contains two inflection points (derivative included as bottom inset) at $P/P_0=0.46$ and 0.87, which is indicative of two populations of internal porosity. The two populations of mesopore restrictions suggests the presence of large interstitial pores defined by the volume between cellular structures connected through two subsets of smaller pores.

The results from the above series of experiments indicate that the silica deposition process occurs throughout the complete volume of the cell to produce a faithful replica of the exterior and interior cellular structures. Based on the featurelessness of silica deposits in select areas, it can be concluded that deposition at pH 3 involves weakly charged monomeric or small oligomeric silicic acid species that interact non-covalently with the crowded biomolecular components comprising the cell. The high fidelity replication and self-limiting characteristics suggest a mechanism where silicic acid is distributed uniformly over and throughout the cell scaffold where it undergoes acid or base catalyzed condensation promoted by the spectrum of proximal functional groups such as protein surface residues. In this manner, the process is inherently self-limiting to form a continuous silica replica throughout the cell. Remarkable is that the silicified cell, although nanostructured, withstands drying and sintering to 550° C. with minimal shrinkage, as shown in FIG. 6. Generally, drying (capillary) and sintering stresses would result in enormous volumetric changes. See C. J. Brinker and G. W. Scherer, *Sol-gel science* (Academic Press, San Diego) (1990). The absence of appreciable shrinkage speaks to the mechanical integrity of the cell-catalyzed silica replica. The absence of primary particles and microporosity reduces greatly both drying and sintering stresses, which scale roughly inversely with particle or pore size. One mechanistic hypothesis consistent with these observations is that at pH 3 where silicic acid monomers and oligomers are uncharged, silicic acid incorporates within the continuous hydrogen bonded water network encompassing cellular surfaces where it becomes locally concentrated and subsequently condensed amphoterically via surface moieties (e.g. acidic and basic protein residues). See T. Coradin et al., *Colloids Surf B* 29, 189 (2003); and R. K. Iler, *The chemistry of silica: solubility, polymerization, colloid and surface properties, and biochemistry* (Wiley, New York) (1979).

In essence, the structural complexity of cells is captured via self-limiting nanoscale replication in a hard material, providing a platform in which to preserve and reconstitute cellular functions. For example, amphiphilic lipid bilayers introduced as liposomes localize (selectively as compared to on the adjoining substrate) on the outer surfaces of CSCs demonstrating that the membrane lipid component could, in principle, be reconstituted. Subsequent, incubation with a lipid diffusible fluorogenic stain used to assess cellular viability indicated retention of some level of enzyme activity; sequestration of the dye (based on esterase cleavage to form a lipid insoluble fluorophore) was observed in CSCs supporting lipid membranes versus calcined CSCs, as shown in FIG. 15c. FIG. 15c is an image of CSC particles supporting lipid layers showing accumulation of esterase fluorogenic products, as indicated by the line labeled "CSC/lipid". The line labeled "CSC/lipid (calc)" shows activity of calcined CSCs supporting lipid bilayers. These initial results provide an avenue to begin to explore CSCs as an alternative route to biocatalyst stabilization where the current state-of-the-art employs pre-fabricated (mesoporous) silicas for subsequent enzyme loading. See U. Hanefeld et al., *Chem Soc Rev* 38, 453 (2008); S. Hudson et al., *Angew Chem Int Ed* 47, 8582 (2008); L. Betancor and H. R. Luckarift, *Trends Biotechnol* 26, 566 (2008); and D. Avnir et al., *J Mater Chem* 16, 1013 (2005). By using this general approach as a starting point, more complex and specific biocatalyst stabilization can be targeted, by stabilizing enzymes and enzyme complexes in their optimized, crowded in vivo configurations.

Figure 18:
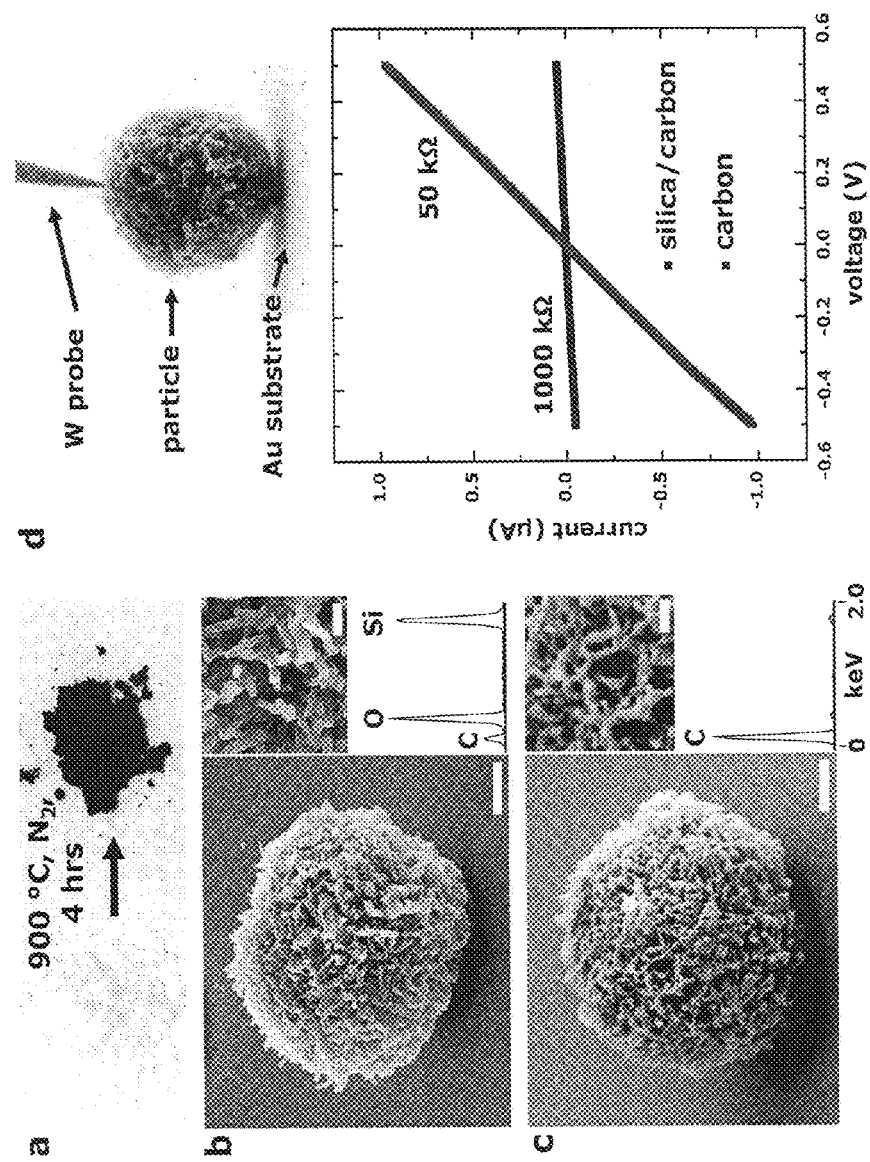
FIG. 18 illustrates shape-preserving carbonization of 4T1 CSCs. Provided are (a) images showing pyrolysis of CSCs produces an opaque powder comprised of particles that have retained cellular structure, shown in (b). Etching of the silica produces a carbon rich replica, as seen in (c). Also provided are (d) in situ electrical characterization of carbonized particles shows a 20 fold decrease in electrical resistance across a particle following silica etching. Scale bars for (b) and (c) panels, 2 μm; insets, 500 nm.

Finally, the ability to replicate both surface and intracellular molecular architectures with silica provides opportunities to investigate shape-preserving chemical transformations of CSCs to other materials, for instance, using approaches analogous to those developed for diatom silica. See K. H. Sandhage et al., *Handbook of Biomineralization: Biomimetic and bioinspired chemistry*, 235 (2007); D. Losic et al., *Adv Mater* 21, 2947 (2009); and Z. Bao et al., *Nature* 446, 172 (2007). Therefore, the ability of CSCs to render porous carbon structures, a class of materials with substantial utility in fuel cell, decontamination, and sensor technologies, was investigated. FIG. 18 illustrates the shape-preserving carbonization of 4T1 CSCs. FIG. 18a shows the pyrolysis of CSCs produces an opaque powder comprised of particles that have retained cellular structure, as shown in FIG. 18c. Etching of the silica produces a carbon rich replica. FIG. 18d shows in situ electrical characterization of carbonized particles shows a 20 fold decrease in electrical resistance across a particle following silica etching. The CSC particles were subjected to high-temperature pyrolysis conditions (900° C., 4 hrs, under $N_2$ atmosphere) which resulted in an opaque powder, as shown in FIG. 18a, with individual particles (carbonized-cell/silica composites, c-CSCs) displaying similar morphologies to that of the starting material, as shown in FIG. 18b. Subsequent dissolution of the silica support (6 M potassium hydroxide (KOH), 4 days) resulted in free-standing carbon particles retaining cellular morphologies, as shown in FIG. 18c. In situ SEM electrical characterization, as shown in FIG. 18d, showed ohmic conductivity through the particles. Representative IV curves for c-CSCs and carbon replicas are shown in the lower panel of FIG. 18d. Note that removal of the insulative silica support decreased particle resistance ~20 fold. These results indicate that the wide heterogeneity of in vitro soft cellular architectures can now be considered for use as a feedstock for most materials processing procedures, including those requiring high temperature and pressure.

Therefore, the present invention provides a simple method to derive functional biomorphic composites, silica "frustules", and carbon replicas from cells, which can allow straightforward customization of structure and function via chemical and genetic engineering. This method does not require pre-infiltration of templating molecules (e.g., cationic polymers) or multistep layer by layer assembly and is distinct from other inorganic biotemplating strategies that simply coat external surfaces to produce hollow shells or low fidelity inverse structures following calcination. See L. Niu et al., *Angew Chem Int Ed* 50, 11688 (2011); O. Paris et al., *MRS Bull* 35, 219 (2010); and M. Dickerson et al., *Chem Rev* 108, 4935 (2008). In contrast to the majority of studies describing cell encapsulation in silica where the primary goal of maintaining cell viability necessitates reaction conditions near neutral pH and cells become physically entrapped within (non-conformal) gels, with the method of the present invention the charge of silicic acid is essentially neutral (pH 3) and thus hydrogen bonding and other non-covalent silica/molecular interactions govern deposition. See C. F. Meunier et al., *J. Colloid Interface Sci.* 342(2), 211 (2010); T. Coradin et al., *Colloids Surf B* 29, 189 (2003); R. K. Iler, *The chemistry of silica: solubility, polymerization, colloid and surface properties, and biochemistry* (Wiley, New York) (1979); and C. Y. Khripin et al., *ACS Nano* 5, 1401 (2011). To date, individual cellular/biomolecular components, peptides, proteins, lipid vesicles, polysaccharides, cytoskeletal filaments, etc. have all been shown to interact with, and often template silica in vitro but with no control over 3D structure. See O. Paris et al., *MRS Bull* 35, 219 (2010); A. Bassindale et al., *J Mater Chem* 19, 7606 (2009); M. Dickerson et al., *Chem Rev* 108, 4935 (2008); and R. K. Iler, *The chemistry of silica: solubility, polymerization, colloid and surface properties, and biochemistry* (Wiley, New York) (1979). Presented on and within a cell, these collective silica/molecular interactions are exploited in the present method under molecularly crowded environments using stable sols (e.g., limited homo-polymerization, no gel formation, etc.) such that deposition is targeted to cell structures, resulting in a process that is inherently conformal and self-limiting due to slow solution silica polymerization kinetics. See R. K. Iler, *The chemistry of silica: solubility, polymerization, colloid and surface properties, and biochemistry* (Wiley, New York) (1979). The generalizability of this method can enable the synthetic production of complex and durable composites and minerals with structural diversity approaching that of natural biomineralizing microorganisms.

Figure 20:
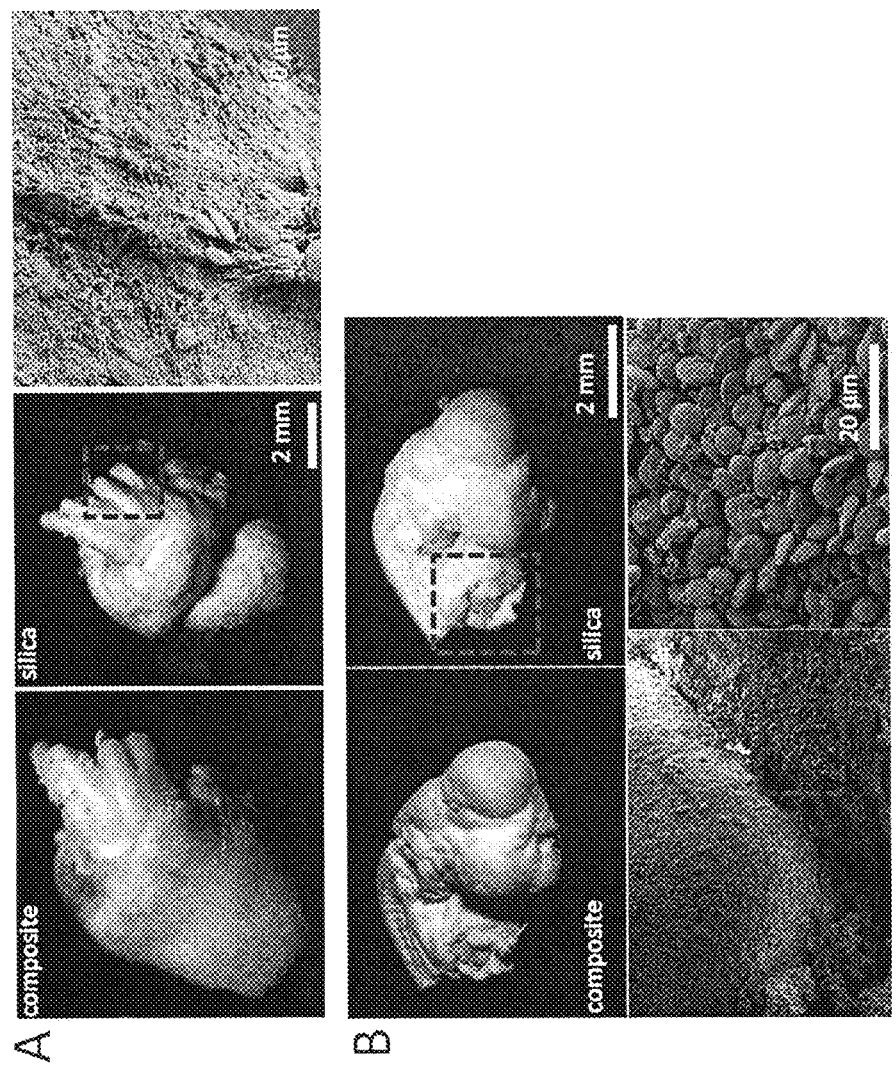
FIG. 20 shows SEM images. Provided are (a) images of a chicken embryo heart before and after silicification; and (b) images of a complete chicken embryo before and after silicification.

Using the methods described above for single cells, the present invention can be used preservation/replication of higher order animal structures such as soft tissue and whole organisms. FIG. 20A shows a chicken embryo heart (box outline is further magnified in right panel). FIG. 20B shows a complete chicken embryo. Silicification takes place over the course of 3-8 days but remarkably, the entire architectural hierarchy of macro-scale features down again to single cells and sub-cellular structures is replicated in silica following calcination at 500° C. for 6-12 hrs, as shown in the right-hand panels of FIGS. 20A and 20B.

The present invention has been described as a method to synthesize cell/silica composites. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A method to synthesize a particle comprising:
   incubating a plurality of cells in a silicic acid solution to provide cell/silica composite particles;
   dehydrating the cell/silica composite particles to provide monodisperse cell/silica composite particles; and
   introducing a lipid layer or a biological material to said monodisperse cell/silica composite particles.

2. The method of claim 1, wherein the plurality of cells comprises mammalian cells, prokaryotic cells, plant cells, cultured cells, tissue, or biological organism.

3. The method of claim 1, wherein the plurality of cells is genetically, chemically, or physically modified.

4. The method of claim 1, further comprising fixing the plurality of cells in a fixative prior to the incubating step.

5. The method of claim 1, wherein the silicic acid solution is osmotically balanced.

6. The method of claim 1, further comprising plating the plurality of cells on a substrate prior to the incubating step.

7. The method of claim 1, further comprising patterning the plurality of cells on a surface prior to the incubating step.

8. The method of claim 1, wherein the plurality of cells are suspended in the silicic acid solution.

9. The method of claim 1, wherein the dehydrating step provides a dry powder.

10. The method of claim 1, wherein the silicic acid solution comprises tetramethoxysilane, tetraethoxysilane, or a mixture thereof.

11. A method to synthesize a particle comprising:
    incubating a plurality of cells in a silicic acid solution to provide cell/silica composite particles;
    dehydrating the cell/silica composite particles to provide monodisperse cell/silica composite particles;
    calcinating the monodisperse cell/silica composite particles at an elevated temperature to provide silica replicas; and
    introducing a lipid layer or a biological material to said silica replicas.

12. The method of claim 11, wherein the elevated temperature is greater than 500° C.

13. The method of claim 11, wherein the biological material of the introducing step comprises an enzyme, ATP, an organelle, or RNA.

14. The method of claim 1, wherein the biological material of the introducing step comprises an enzyme, ATP, an organelle, or RNA.

15. The method of claim 1, wherein the introducing step comprises localizing a lipid bilayer on an outer surface of said cell/silica composite particles.

16. The method of claim 11, wherein the plurality of cells comprises mammalian cells, prokaryotic cells, plant cells, cultured cells, tissue, or biological organism.

17. The method of claim 11, further comprising fixing the plurality of cells in a fixative prior to the incubating step.

18. The method of claim 11, wherein the silicic acid solution is osmotically balanced.

19. The method of claim 11, wherein the introducing step comprises localizing a lipid bilayer on an outer surface of said cell/silica composite particles.

20. A method to synthesize a particle comprising:
    incubating a plurality of cells in a silicic acid solution to provide cell/silica composite particles;
    washing the cell/silica composite particles; and
    introducing a lipid layer to an outer surface of said cell/silica composite particles.

* * * * *